(12) United States Patent
Aali

(10) Patent No.: US 7,863,495 B2
(45) Date of Patent: Jan. 4, 2011

(54) DRESSING SUBSTRATE

(75) Inventor: Adel Aali, Irvine, CA (US)

(73) Assignee: Aalnex, Inc., Irvine, CA (US)

( * ) Notice: Subject to any disclaimer, the term of this patent is extended or adjusted under 35 U.S.C. 154(b) by 145 days.

(21) Appl. No.: 11/441,702

(22) Filed: May 26, 2006

(65) Prior Publication Data

US 2007/0161938 A1    Jul. 12, 2007

Related U.S. Application Data

(63) Continuation-in-part of application No. 11/409,364, filed on Apr. 20, 2006, now Pat. No. 7,622,629.

(60) Provisional application No. 60/758,389, filed on Jan. 12, 2006.

(51) Int. Cl.
*A61F 13/00* (2006.01)

(52) U.S. Cl. .............................. 602/42; 602/54; 602/58; 128/888; 128/889

(58) Field of Classification Search ............. 129/41–43, 129/48; 128/888, 889; 604/304–308; 602/41–59
See application file for complete search history.

(56) References Cited

U.S. PATENT DOCUMENTS

| | | | | |
|---|---|---|---|---|
| 2,273,873 A | * | 2/1942 | Klein | 128/888 |
| 2,305,289 A | | 12/1942 | Coburg | |
| 2,367,690 A | | 1/1945 | Purdy | 128/888 |
| 2,443,140 A | | 6/1948 | Larsen | 128/888 |
| 2,443,481 A | | 6/1948 | Sene | 128/888 |
| 3,026,874 A | | 3/1962 | Stevens | 604/305 |
| 3,334,626 A | | 8/1967 | Schimmel | 128/888 |
| 4,023,569 A | | 5/1977 | Warnecke et al. | 128/154 |
| 4,181,127 A | | 1/1980 | Linsky et al. | 602/43 |
| 4,212,296 A | | 7/1980 | Schaar | 602/42 |

(Continued)

FOREIGN PATENT DOCUMENTS

DE    1963375 A1    6/1971

(Continued)

OTHER PUBLICATIONS

USPTO Examiner Interview Summary and Non-Final Office Action for U.S. Appl. No. 11/303,463, 9 pages (mailed Aug. 20, 2009).

(Continued)

*Primary Examiner*—Kim M Lewis
(74) *Attorney, Agent, or Firm*—Jones Day; Nicola A. Pisano; Jaime D. Choi

(57) ABSTRACT

A wound shield to manage repetitive access stress may include a conformable substrate to circumscribe a wound. Any suitable dressing may be secured to the conformable substrate providing separation between the wound and the dressing. The wound substrate may provide a site for attachment of adhesive dressings to shield the patient's skin from the pain of repetitive access and or removal of the dressings. A conformable substrate may be composed of one or more layers of any suitable material and may include adhesive on one or more surfaces to secure the substrate to the wound site and or to secure the dressing to the conformable substrate. A wound substrate may include strong adhesive to secure the substrate to the patients skin. The conformable wound substrate will be formed of any suitable non-absorbent material to permit long term application adjacent a wound. Thus many dressings may be applied and removed from a single wound substrate shielding the patient's skin from repetitive insult. A wound substrate according to the present disclosure may also be combined with a conformable frame to provide exudate management and or pressure distribution around a wound.

13 Claims, 14 Drawing Sheets

U.S. PATENT DOCUMENTS

| | | | | |
|---|---|---|---|---|
| 4,252,120 | A | 2/1981 | Carpenter | |
| 4,726,364 | A | 2/1988 | Wylan | 602/44 |
| 4,969,881 | A | 11/1990 | Viesturs | |
| 5,020,547 | A | 6/1991 | Strock | |
| 5,060,662 | A * | 10/1991 | Farnswoth, III | 128/888 |
| 5,086,763 | A | 2/1992 | Hathman | |
| 5,101,837 | A | 4/1992 | Perrin | 128/888 |
| 5,215,539 | A | 6/1993 | Schoolman | |
| 5,264,218 | A | 11/1993 | Rogozinski | |
| 5,356,372 | A | 10/1994 | Donovan et al. | 602/58 |
| 5,376,067 | A | 12/1994 | Daneshvar | 602/58 |
| 5,449,340 | A | 9/1995 | Tollini | |
| 5,456,660 | A | 10/1995 | Reich et al. | |
| 5,478,308 | A | 12/1995 | Cartmell et al. | |
| 5,527,265 | A | 6/1996 | McKeel | 602/6 |
| 5,533,962 | A | 7/1996 | Peterman et al. | 602/54 |
| 5,603,946 | A | 2/1997 | Constantine | |
| 5,694,723 | A | 12/1997 | Parker | 602/42 |
| 5,695,456 | A | 12/1997 | Cartmell et al. | |
| 5,702,356 | A | 12/1997 | Hathman | |
| 5,817,145 | A | 10/1998 | Augustine et al. | 607/98 |
| 5,843,011 | A | 12/1998 | Lucas | |
| 5,885,237 | A | 3/1999 | Kadash et al. | |
| 5,891,074 | A | 4/1999 | Cesarczyk | 602/42 |
| 5,947,914 | A | 9/1999 | Augustine | 602/2 |
| 5,954,680 | A | 9/1999 | Augustine | 602/42 |
| 5,961,480 | A | 10/1999 | Augustine | 602/41 |
| 5,964,721 | A | 10/1999 | Augustine | 602/2 |
| 5,986,163 | A | 11/1999 | Augustine | 712/204 |
| 6,000,403 | A | 12/1999 | Cantwell | |
| 6,005,159 | A | 12/1999 | Spier | 602/42 |
| 6,010,527 | A | 1/2000 | Augustine et al. | 607/96 |
| 6,013,097 | A | 1/2000 | Augustine et al. | 607/96 |
| 6,043,408 | A | 3/2000 | Geng | 602/58 |
| 6,071,254 | A | 6/2000 | Augustine | 602/2 |
| 6,071,304 | A | 6/2000 | Augustine et al. | 607/96 |
| 6,080,189 | A | 6/2000 | Augustine et al. | 607/96 |
| 6,093,160 | A | 7/2000 | Augustine et al. | 602/2 |
| 6,095,922 | A | 8/2000 | Friedrichsen et al. | 464/24 |
| 6,095,992 | A | 8/2000 | Augustine | 464/24 |
| 6,110,197 | A | 8/2000 | Augustine et al. | 607/108 |
| 6,113,561 | A | 9/2000 | Augustine | 602/2 |
| 6,143,945 | A | 11/2000 | Augustine et al. | 602/41 |
| 6,168,800 | B1 | 1/2001 | Dobos et al. | |
| 6,213,965 | B1 | 4/2001 | Augustine et al. | 602/2 |
| 6,217,535 | B1 | 4/2001 | Augustine | 602/2 |
| 6,235,047 | B1 | 5/2001 | Augustine et al. | 607/96 |
| 6,267,740 | B1 | 7/2001 | Augustine et al. | 602/2 |
| 6,283,931 | B1 | 9/2001 | Augustine | 602/2 |
| 6,293,917 | B1 | 9/2001 | Augustine | 602/2 |
| 6,320,093 | B1 | 11/2001 | Augustine et al. | 602/41 |
| 6,406,448 | B1 | 6/2002 | Augustine | 602/2 |
| 6,407,307 | B1 | 6/2002 | Augustine | 602/42 |
| 6,419,651 | B1 | 7/2002 | Augustine | 602/2 |
| 6,420,622 | B1 | 7/2002 | Johnston et al. | 602/41 |
| 6,420,623 | B2 | 7/2002 | Augustine et al. | 602/41 |
| 6,423,018 | B1 | 7/2002 | Augustine | 602/2 |
| 6,426,066 | B1 | 7/2002 | Najafi et al. | |
| 6,436,063 | B1 | 8/2002 | Augustine et al. | 602/2 |
| 6,440,156 | B1 | 8/2002 | Augustine et al. | 607/96 |
| 6,458,109 | B1 | 10/2002 | Henley et al. | |
| 6,465,708 | B1 | 10/2002 | Augustine | 602/42 |
| 6,468,295 | B2 | 10/2002 | Augustine et al. | 607/96 |
| 6,485,506 | B2 | 11/2002 | Augustine | 607/96 |
| 6,528,697 | B1 | 3/2003 | Knutson et al. | 602/54 |
| 6,569,189 | B1 | 5/2003 | Augustine et al. | 607/96 |
| 6,570,050 | B2 | 5/2003 | Augustine et al. | 602/41 |
| 6,573,420 | B2 | 6/2003 | Stapf et al. | 602/42 |
| 6,580,012 | B1 | 6/2003 | Augustine et al. | 602/42 |
| 6,585,670 | B2 | 7/2003 | Augustine et al. | 602/2 |
| 6,589,270 | B2 | 7/2003 | Augustine | 607/96 |
| 6,605,051 | B2 | 8/2003 | Augustine | 602/2 |
| 6,626,891 | B2 | 9/2003 | Ohmstede | |
| 6,641,601 | B1 | 11/2003 | Augustine et al. | 607/96 |
| 6,653,520 | B1 | 11/2003 | Mouton | 602/45 |
| 6,685,681 | B2 | 2/2004 | Lockwood et al. | |
| 6,716,235 | B2 | 4/2004 | Augustine et al. | 607/96 |
| 6,840,915 | B2 | 1/2005 | Augustine | 602/2 |
| 6,960,181 | B2 | 11/2005 | Stevens | |
| 6,974,428 | B2 | 12/2005 | Knutson et al. | 602/2 |
| 7,012,170 | B1 | 3/2006 | Tomaioulo | |
| 7,074,982 | B2 * | 7/2006 | Knutson et al. | 602/42 |
| 7,112,712 | B1 | 9/2006 | Ancell | |
| 7,118,545 | B2 | 10/2006 | Boyde | 602/79 |
| 7,122,046 | B2 | 10/2006 | Augustine et al. | 607/96 |
| 7,122,712 | B2 | 10/2006 | Lutri et al. | 602/43 |
| 7,135,606 | B1 | 11/2006 | Dozier et al. | 602/57 |
| 7,176,343 | B2 | 2/2007 | Schlussel | |
| 7,183,454 | B1 * | 2/2007 | Rosenberg | 602/43 |
| 7,276,051 | B1 | 10/2007 | Henley et al. | |
| 7,601,129 | B2 | 10/2009 | Aali | |
| 7,622,629 | B2 | 11/2009 | Aali | |
| 2002/0007136 | A1 | 1/2002 | Narula et al. | 602/46 |
| 2002/0026133 | A1 | 2/2002 | Augustine et al. | 607/2 |
| 2002/0029010 | A1 * | 3/2002 | Augustine et al. | 602/41 |
| 2003/0036715 | A1 | 2/2003 | Knutson et al. | |
| 2003/0088201 | A1 | 5/2003 | Darcey | 602/44 |
| 2004/0249328 | A1 | 12/2004 | Linnane et al. | 602/43 |
| 2005/0004500 | A1 | 1/2005 | Rosser et al. | |
| 2005/0010153 | A1 | 1/2005 | Lockwood et al. | |
| 2005/0070835 | A1 | 3/2005 | Joshi | |
| 2005/0107732 | A1 | 5/2005 | Boyde | |
| 2005/0113731 | A1 | 5/2005 | Qvist | 602/48 |
| 2005/0148921 | A1 | 7/2005 | Hsu | 602/48 |
| 2005/0222528 | A1 | 10/2005 | Weston | |
| 2006/0064049 | A1 | 3/2006 | Marcussen | 602/42 |
| 2006/0116620 | A1 | 6/2006 | Oyaski | |
| 2006/0189909 | A1 | 8/2006 | Hurley et al. | 602/41 |
| 2006/0235347 | A1 | 10/2006 | Aali | |
| 2006/0253089 | A1 | 11/2006 | Lin | 604/301 |
| 2007/0142757 | A1 | 6/2007 | Aali | |
| 2007/0142761 | A1 | 6/2007 | Aali | |
| 2007/0161937 | A1 | 7/2007 | Aali | |
| 2007/0191754 | A1 | 8/2007 | Aali | |

FOREIGN PATENT DOCUMENTS

| | | |
|---|---|---|
| EP | 0117714 A2 | 9/1984 |
| WO | WO 85/01439 A1 | 4/1985 |
| WO | WO 96/15745 A1 | 5/1996 |
| WO | WO98/53778 | 12/1998 |

OTHER PUBLICATIONS

USPTO Non-Final Office Action for U.S. Appl. No. 11/107,452, 11 pages (mailed Mar. 17, 2009).

USPTO Final Office Action for U.S. Appl. No. 11/107,452, 8 pages (mailed Sep. 19, 2008).

USPTO Non-Final Office Action for U.S. Appl. No. 11/107,452, 7 pages (mailed Dec. 4, 2007).

USPTO Non-Final Office Action for U.S. Appl. No. 11/107,452, 8 pages (mailed May 31, 2007).

USPTO Non-Final Office Action for U.S. Appl. No. 11/707,464, 11 pages (mailed Apr. 14, 2009).

USPTO Non-Final Office Action for U.S. Appl. No. 11/707,464, 8 pages (mailed Jun. 27, 2008).

USPTO Notice of Allowance for U.S. Appl. No. 11/303,155, 5 pages (mailed Jun. 12, 2009).

USPTO Non-Final Office Action for U.S. Appl. No. 11/303,155, 7 pages (mailed Jan. 8, 2009).

USPTO Non-Final Office Action for U.S. Appl. No. 11/303,155, 9 pages (mailed Jul. 14, 2008).

USPTO Notice of Allowance for U.S. Appl. No. 11/409,364, 7 pages (mailed Jul. 10, 2009).

USPTO Final Office Action for U.S. Appl. No. 11/409,364, 9 pages (mailed Mar. 10, 2009).

USPTO Non-Final Office Action for U.S. Appl. No. 11/409,364, 7 pages (mailed May 22, 2008).

USPTO Advisory Action for U.S. Appl. No. 11/409,364, 3 pages (mailed Apr. 8, 2008).

USPTO Final Office Action for U.S. Appl. No. 11/409,364, 7 pages (mailed Nov. 30, 2007).

USPTO Non-Final Office Action for U.S. Appl. No. 11/409,364, 7 pages (mailed May 31, 2007).

USPTO Non-Final Office Action for U.S. Appl. No. 11/303,463, 10 pages (mailed Mar. 17, 2009).

USPTO Final Office Action for U.S. Appl. No. 11/303,463, 9 pages (mailed Dec. 26, 2008).

USPTO Non-Final Office Action for U.S. Appl. No. 11/303,463, 11 pages (mailed Mar. 18, 2008).

USPTO Final Office Action for U.S. Appl. No. 11/107,452, 8 pages (mailed Dec. 24. 2009).

USPTO Final Office Action for U.S. Appl. No. 11/707,464, 9 pages (mailed Dec. 24, 2009).

* cited by examiner

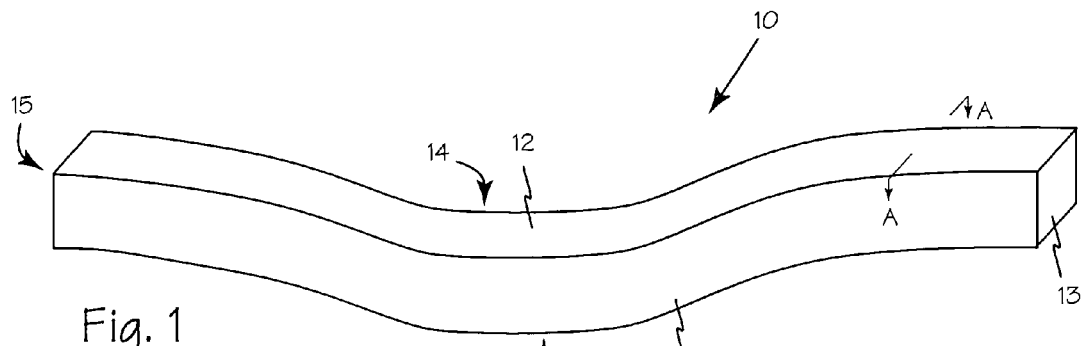
Fig. 1
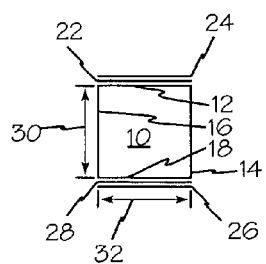
Fig. 2
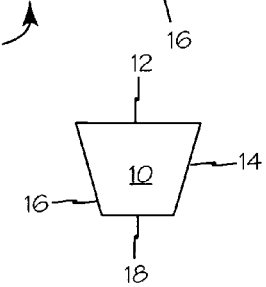
Fig. 3
Fig. 4
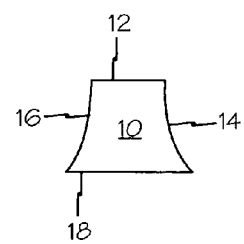
Fig. 5
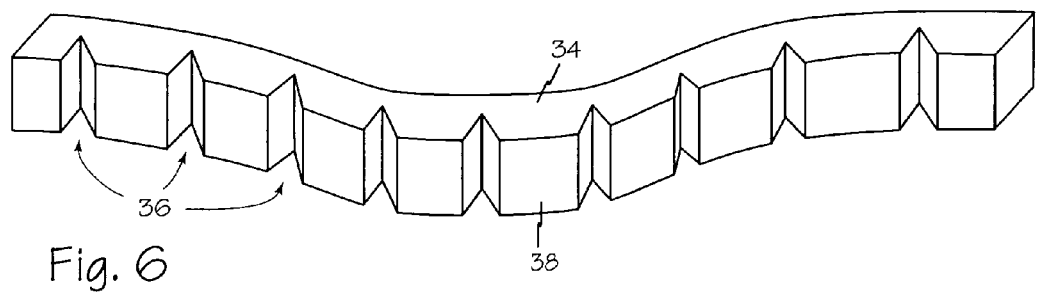
Fig. 6
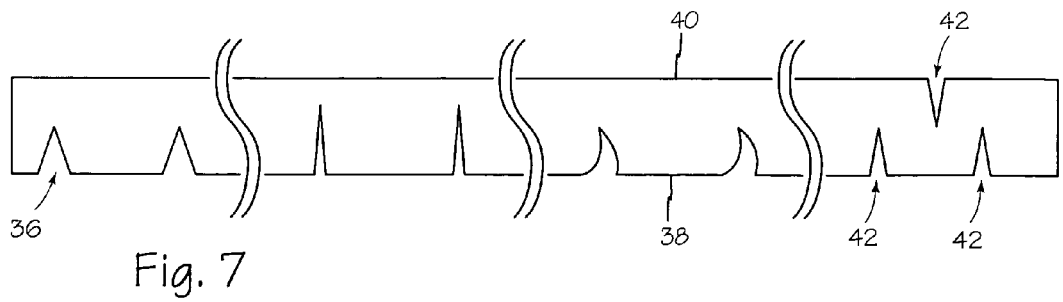
Fig. 7

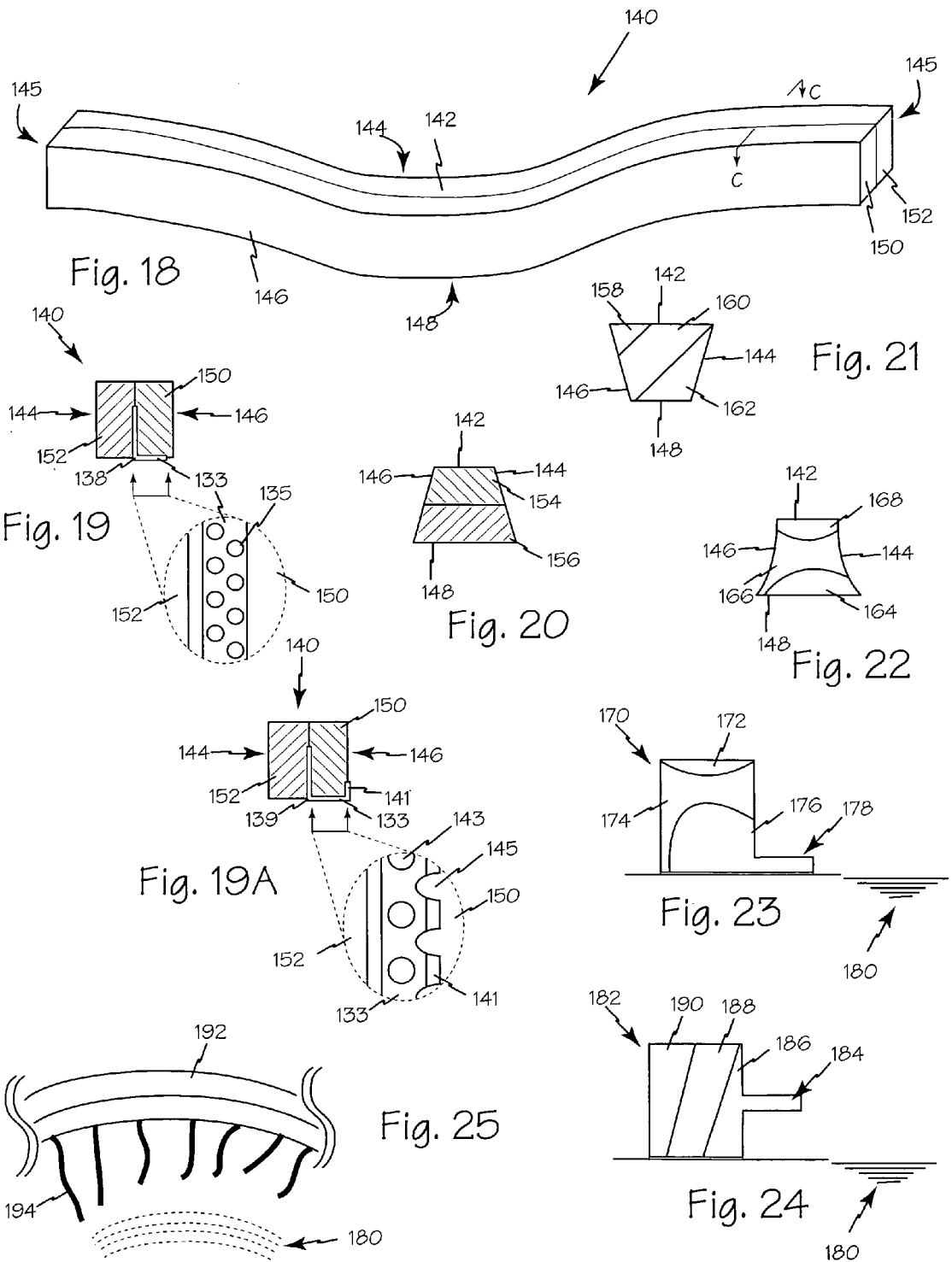

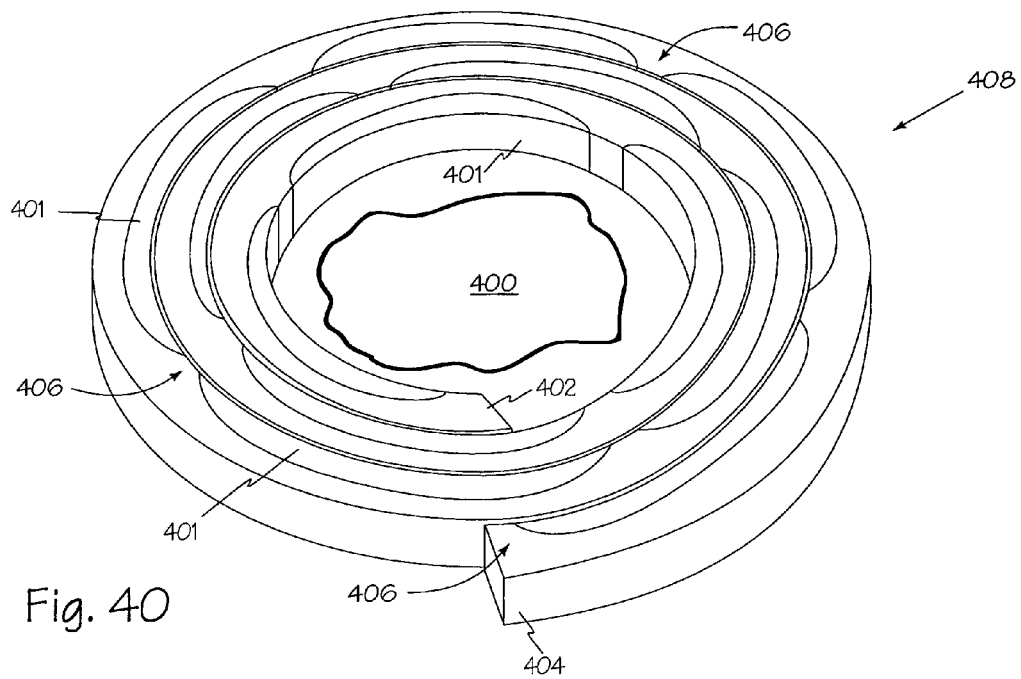
Fig. 40
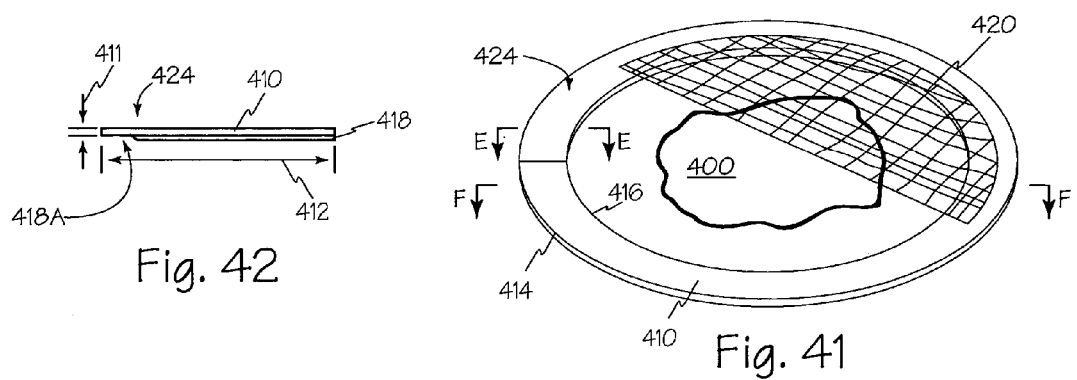
Fig. 42
Fig. 41
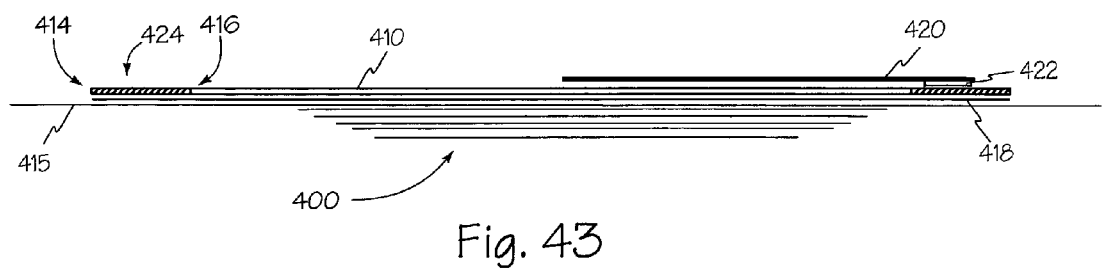
Fig. 43

DRESSING SUBSTRATE

RELATED APPLICATIONS

This application is a continuation-in-part of U.S. Utility patent application Ser. No. 11/409,364 filed Apr. 20, 2006, now U.S. Pat. No. 7,622,629 which claims priority from copending U.S. Provisional Patent Application 60/758,389 filed Jan. 12, 2006 and copending U.S. Utility patent application Ser. No. 11/303,463 filed Dec. 15, 2005.

FIELD OF THE INVENTIONS

The inventions described below relate to the field of wound care and specifically to conformable dressing accessories.

BACKGROUND OF THE INVENTIONS

Wounds occur when the integrity of any tissue is compromised, affecting one or more layers of skin or underlying tissue. Wounds may be caused by an act, surgical procedure, an infectious disease or an underlying condition. Examples of open wounds include punctures, abrasions, cuts, lacerations and burns. Chronic wounds are also common ailments and include pressure ulcers, diabetic ulcers, arterial ulcers, venous ulcers or combination of all the above. Despite much progress made in the wound care industry, an efficient and effective method and apparatus for protecting the wound and adjacent tissue from injurious contacts and or stimulation is not readily available.

Injurious contacts and or stimulation may result from various causes, ranging from clothing or bed sheets brushing or adhering to wound surfaces or adjacent tissue to adherence of wound dressing to the wound and or adjacent sensitive tissue. Repetitive access or removal of adhesive dressings from sensitive skin and other tissue surrounding a wound is very stressful to patients and may lead to deleterious consequences for the patient. It is reported that in certain circumstances patients are administered morphine to withstand the pain caused from dressing removal, especially with wounds having a large surface area.

Wounds are generally covered to prevent contamination and resulting infection. Wounds may also be covered for other reasons, including retaining moisture and absorption of exudate. Wound covering has traditionally consisted of application of dressings that are in direct contact with the wound.

Wound coverings may use adhesive to secure the dressings over a wound. In many cases the tissue surrounding a wound may be as sensitive, or more sensitive to pain than the wound site. This may be particularly true in elderly patients whose skin is generally more delicate.

What is needed is a method and apparatus for dressing wounds or other injuries providing a temporary substrate to shield sensitive tissue adjacent a wound that is conformable, adjustable and flexible to control contact between the dressing and the surface of the wound, permit management of exudate from the wound, improve the environment immediately adjacent the wound and provide pressure relief for the wound.

SUMMARY

A wound shield to manage repetitive access stress may include a conformable substrate to circumscribe a wound. Any suitable dressing may be secured to the conformable substrate providing separation between the wound and the dressing. The wound substrate may provide a site for attachment of adhesive dressings to shield the patient's skin from the pain of repetitive access and or removal of the dressings. A conformable substrate may be composed of one or more layers of any suitable material and may include adhesive on one or more surfaces to secure the substrate to the tissue surrounding the wound and or to secure the dressing to the conformable substrate.

A wound substrate may include strong adhesive to secure the substrate to the patients skin. The conformable wound substrate will be formed of any suitable non-absorbent material to permit long term application adjacent a wound. Thus many dressings may be applied and removed from a single wound substrate shielding the patient's skin from repetitive insult. A wound substrate according to the present disclosure may also be combined with a conformable frame to provide benefits such as exudate management and or pressure distribution around a wound.

In another aspect of the present disclosure, a conformable frame may be formed of material for absorbing wound exudate. Exudate absorbing material may also be one of two or more layers of material forming the conformable frame. The layers may be arranged to keep the exudate absorbing layer at some selected distance from a patients skin.

A wound shield for dynamic exudate management may include two or more layers of material. One layer of the two or more layers of material may be a wicking or conduit material that draws exudate from the wound and transports the exudate to any suitable media for exudate storage. The exudate storage may be one or more layers of a dressing covering the wound site, or it may be a removable reservoir.

A wound shield for exudate management may also include an exterior membrane to permit exudate transfer out of the wound space. A wound shield including an exterior membrane may also include an exudate collection apparatus surrounding the wound shield for collecting and removing exudate from the wound shield and from the patient.

A wound shield for exudate management may also include one or more reclosable or self-closing apertures in the conformable frame to enable exudate management. The exudate aperture may be formed in the conformable frame or in a connector for securing the ends of a conformable frame. The exudate aperture may be engaged as often as necessary for suitable wound care.

A wound shield may include a conformable frame to circumscribe a wound. Any suitable dressing may be secured over the conformable frame, the conformable frame providing separation between the wound and the dressing. The wound frame may provide pressure relief around a wound or pressure sore to permit healing, allow compression for venous ulcers, retain moisture within the wound environment, absorb exudate, relieve pain and trauma associated with dressing removal, allow debridement and application of topical medications and or other compounds or chemicals, accelerate healing and facilitate monitoring of wounds. A conformable frame may be composed of one or more layers of any suitable material and may include adhesive on one or more surfaces to secure the frame to the tissue surrounding the wound, to secure the frame to itself and or any suitable closure element and or to secure the dressing to the conformable frame. A wound shield may be used for humans or any suitable animal.

A conformable substrate and or a wound shield according to the present disclosure may be wrapped one or more times around a wound site in a spiral to seal the wound site and provide improved pressure relief. This method of application requires no cutting or measuring and may result in one or more circumferential wraps of the wound. By wrapping multiple times around a wound the conformable substrate and or the conformable frame are contacting more area of the patients skin in increasing distance from the wound site providing improved pressure relief and broader skin protection. The multiple wraps of the conformable frame may also include exudate absorbent material increasing the capacity of the conformable element and or cover bandage to absorb and store exudate.

A wound shield according to the present disclosure may be a simple, versatile, inexpensive and readily applicable apparatus and method for wound protection. It may include a conformable wound-protecting frame that may conform to the specific contour and size of any wound and may be used with any suitable dressing. A wound shield prevents foreign objects such as clothing, dressings and other such items from contacting the wound. Cotton gauze or other suitable dressing may be placed on or engage a wound protecting frame to completely protect the wound from harmful contact with any object. Alternatively, special covers, seals, and or lids may be placed on the wound shield to control moisture, simplify wound monitoring and debridement and application of medications.

A wound shield according to the present disclosure may adhere to skin surrounding a wound via adhesive applied to a surface of the wound-protecting frame to engage the skin. Medical grade, hypoallergenic adhesives are preferred, although any suitable adhesive may be used such as rubber-based, acrylic, vinyl ether and suitable pressure-sensitive adhesives. For their obvious advantages, adhesives that adhere to body hair less than their conventional counterparts are preferred. Adhesives may also be added to one or more surfaces of a wound-protecting frame not in contact with skin to engage any suitable dressing, cover, lid or any other suitable closure. Alternatively, no adhesive is used with the wound shield, and the wound shield is retained in place by the pressure applied from the dressing wrapped around the wound.

A conformable wound shield frame and or conformable substrate may be provided in any suitable dispenser configuration. For example, the conformable frame and or substrate may be wound around a reel and placed in a dispenser that can be efficiently stored. When needed, the conformable frame and or the substrate may be fed out of the dispenser, and cut to desired lengths. Alternatively, a conformable substrate or a wound-protecting frame may be supplied in a sheet form and cut to the desired length and width. Moreover, the conformable frame or conformable substrate may be prepackaged in several long strips with various or equal widths that may be cut to desirable lengths.

In use, a conformable frame is placed around a wound, creating a boundary and providing a plane separate from the plane of the wound to support the dressing. The conformable frame may be used with any suitable closure to engage the ends of the conformable frame and encircle a wound.

A wound shield according to the present disclosure may be fully deformable to conform to specific contours of any wound located on any surface of a body. It may be cut to a desirable length to enclose all or any portion of the perimeter of any wound, regardless of shape and size. In addition, the conformable frame may be made of inexpensive and yet effective material.

Any suitable dressing may be used in conjunction with the conformable frame, and may range from inexpensive, commonly used cotton gauze to more costly and sophisticated dressings, including for example, those constructed from transparent and or multi-layered material with qualities such as exudate absorption, bacteria impermeability and controlled air and or moisture permeability. Health care professionals may mix and match various dressings without restriction to complex and/or costly non-contact dressings.

A wound shield according to the present disclosure has sufficient rigidity to prevent injurious contacts to the wound, including those caused by dressing adhering to the wound surface. The conformable frame prevents contact to wounds regardless of their size or location with any suitable dressing.

A wound shield according to the present disclosure may be used for swift and effective wound debridement using any suitable technique. For example, a wound shield may be used to create a controlled space adjacent a wound for biological debridement, use of maggots or other suitable techniques. Alternatively, mechanical and or chemical debridement may also be effected within the controlled space. Surgical debridement may also be performed without removing the conformable frame from around the wound. The wound shield minimizes wound and peri-wound disturbance by avoiding repetitive dressing removals with the associated wound surface disturbance.

A wound shield including a conformable frame to circumscribe a wound may also include a circulating system for circulating any suitable fluid to maintain a desired environment. Any suitable dressing may be secured over the conformable frame providing separation between the wound and the dressing. The wound frame may provide pressure relief around a wound or pressure sore to permit healing. A conformable frame may be composed of one or more layers of any suitable material and may include adhesive on one or more surfaces to secure the frame to the wound site and or to secure the dressing to the conformable frame.

Exudate as used in this application may also include any solid or liquid produced by the patients body, or applied to or into a patients body that sloughs, falls, flows, or is discharged from a wound, the wound site or the tissue surrounding the wound.

BRIEF DESCRIPTION OF THE DRAWINGS

FIG. 1 is a perspective view of a conformable frame according to the present disclosure.

FIG. 2 is a cross section of the conformable frame of FIG. 1 taken along A-A.

FIG. 3 is an alternate cross section of the conformable frame of FIG. 1.

FIG. 4 is another alternate cross section of the conformable frame of FIG. 1.

FIG. 5 is a still alternate cross section of the conformable frame of FIG. 1.

FIG. 6 is a perspective view of an alternate conformable frame according to the present disclosure.

FIG. 7 is a top view of a conformable frame similar to FIG. 6 illustrating alternative configurations.

FIG. 18 is a perspective view of an alternate deformable wound frame according to the present disclosure.

FIG. 19 is a cross section of the conformable frame of FIG. 18 taken along C-C.

FIG. 19A is a cross section of the conformable frame of FIG. 18 taken along C-C with an alternate scaffold.

FIG. 20 is an alternate cross section of the conformable frame of FIG. 18.

FIG. 21 is another alternate cross section of the conformable frame of FIG. 18.

FIG. 22 is yet another alternate cross-section of the conformable frame of FIG. 18.

FIG. 23 is an alternate cross section of the conformable frame of FIG. 18 with a wicking element.

FIG. 24 is another alternate cross section of the conformable frame of FIG. 23.

FIG. 25 is a perspective view of an alternate conformable frame according to the present disclosure.

FIG. 40 is a perspective view of an alternate deformable wound frame with exudate absorbent areas, spiral wrapped according to the present disclosure.

FIG. 41 is a perspective view of a conformable wound substrate according to the present disclosure.

FIG. 42 is a cross section of the conformable substrate of FIG. 41 taken along E-E.

FIG. 43 is a cross section of the conformable substrate and wound of FIG. 41 taken along F-F.

DETAILED DESCRIPTION OF THE INVENTIONS

Figure 8:
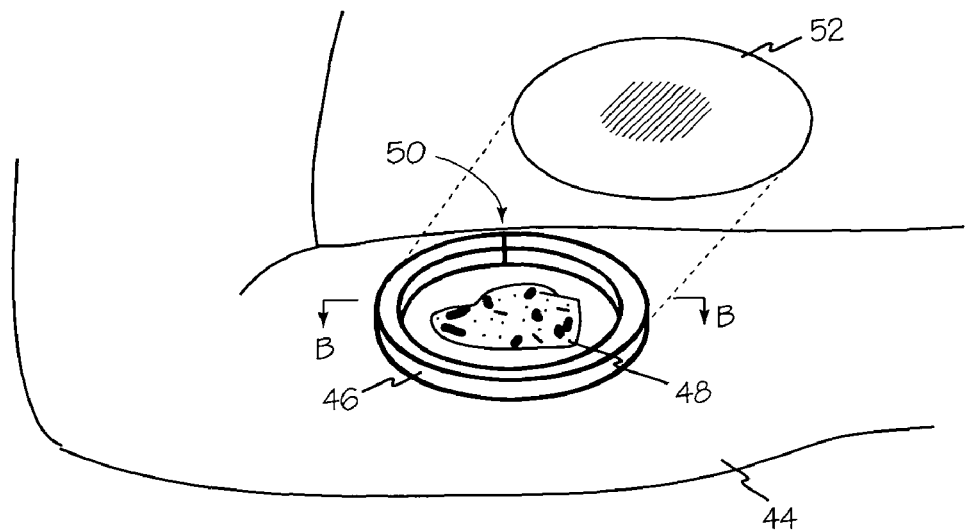
FIG. 8 is a perspective view of a conformable frame surrounding a small wound on the forearm.

Referring to FIG. 1 and FIG. 2, conformable frame 10 provides perimeter protection for a wound and may conform to specific contours of the wound site. Conformable frame 10 includes exterior side 14 facing away from the wound and interior side 16 facing the wound, superficial surface 12 for engaging dressings and cutaneous surface 18 in contact with the patient's skin, or any other dressing or apparatus in contact with the patient's skin. Any suitable adhesive may be applied to cutaneous surface 18 and or superficial surface 12 such as adhesive 28 and 22 respectively. A strip or a film, such as film 24 and 26, may also cover adhesive layers 22 and 28 respectively, that can be peeled off at the time of use. Adhesive 28 secures conformable frame 10 to skin surrounding a wound, or in some applications, to a dressing or apparatus that is in contact with the patient's skin. When applied to superficial surface 12, adhesive layer 22 may engage a dressing or other suitable cover to conformable frame 10.

In use, conformable frame 10 includes a first end 13 and a second end 15. When positioned around a wound, first end 13 and second end 15 may be engaged to completely circumscribe the wound as shown in FIG. 8. An adhesive or other suitable material may be applied to first end 13 and or second end 15 to secure the engagement of first end 13 and second end 15. Conformable frame 10 may have any suitable cross-section as shown in FIG. 2 including height 30 and width 32. The size of a wound site to be circumscribed may require height 30 and width 32 to be available in different dimensions. Larger wounds may have a dressing sag and inadvertently contact the wound. First end 13 and or second end 15 may be cut, preshaped or scored such that first end 13 and or second end 15 are not perpendicular to the interior and exterior surfaces, or the superficial and cutaneous surfaces. The angle between the end surface and the side of the conformable frame may be selected to optimize the curvature of the conformable frame, or to increase the mating surface areas of the ends.

Conformable frame 10 may be constructed from any suitable material capable of deformation in the X and or Y and or Z-axes. Silicone is one example of such material, as it is both rigid and deformable. Polymers such as polypropylene, polyethylene and polyurethane may also be used to form a deformable, and yet rigid wound protector. Depending on its specific use, additional features of a wound shield may include impermeability or controlled permeability to water, bacteria and air, and absorption of fluids exuding from the wound bed. A wound shield according to the present disclosure may also include a selectable moisture vapor transmission rate (MVTR). Polyurethane foam may be used to form a wound-protecting frame for its ability to absorb exudates.

Referring now to FIGS. 3-5, alternative cross sections may be used. Any suitable cross section may be used.

Referring now to FIG. 6, alternatively, a conformable frame such as conformable frame 34 may also include a plurality of grooves, cuts or slots such as grooves 36, positioned in either the wound or exterior side such as exterior side 38. Grooves 36 may increase flexibility of conformable frame 34 when constructed of material that may not have sufficient inherent flexibility to allow appropriate conformability. Grooves 36 may be cut or otherwise formed in conformable frame 34 using any suitable technique.

Referring now to FIG. 7, alternate configurations of grooves 36 are illustrated for example. Any suitable geometry may be used for grooves 36. Grooves or slots or cuts such as cuts 42 may also be combined in exterior side 38 as well as wound side 40 for increased flexibility.

Figure 9:
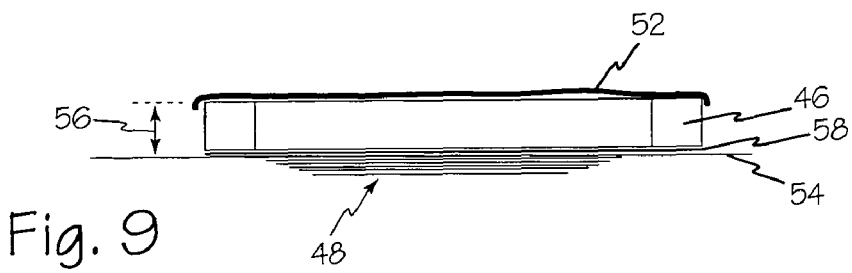
FIG. 9 is a cross section of the conformable frame and dressing on the wound of FIG. 8.

Referring now to FIG. 8 and FIG. 9, conformable frame 46 may be superficially applied to any injured surface of a patient such as forearm 44 using adhesive 58. Conformable frame 46 circumscribes wound 48. First end 13 and second end 15 engage at plane 50. When dressing 52 is used to promote healing of wound 48, conformable frame 46 prevents dressing 52 from contacting wound 48 by creating a separation 56 between dressing 52 and wound plane or skin surface 54. Separation 56 is controlled by height 30 of the conformable frame.

As briefly described above, dressing 52 may be any suitable dressing. Dressing 52 may also include adhesive along its perimeter or longitudinal and/or its transverse lengths, so to facilitate its adherence to skin surrounding conformable frame 46. Alternatively, dressing 52 may be wrapped around the arm or other body parts on which wound 48 is situated, or dressing 52 may be sized or cut to size to engage only conformable frame 46. Dressings such as dressing 52 may have any suitable MVTR parameters.

Figure 10:
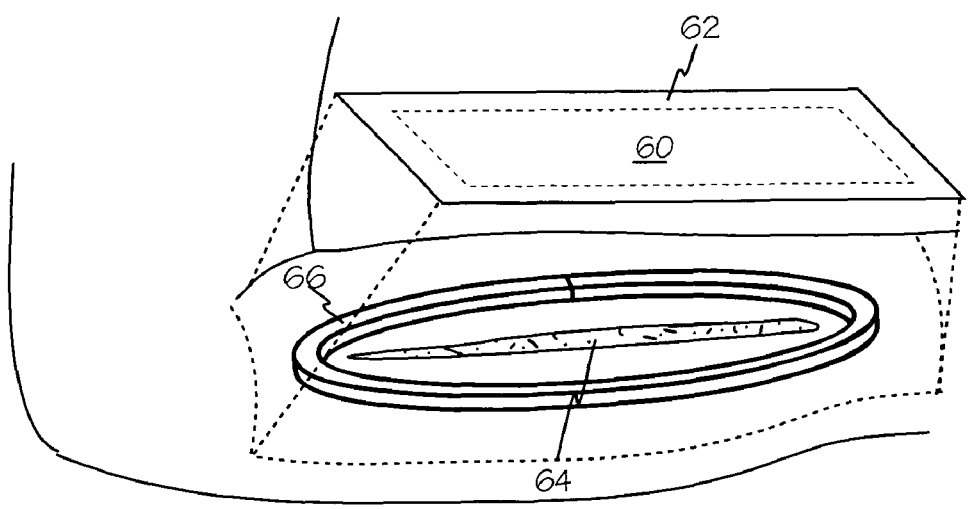
FIG. 10 is a perspective view of a conformable frame surrounding a long, oddly shaped laceration on the forearm.

Referring now to FIG. 10, dressing 60 may be used to secure conformable frame 66 around wound 64, which is a long, narrow, oddly shaped laceration. Adhesive may be included around perimeter 62 of dressing 60. One or more dressing such as dressing 60 may be used. Dressing 60 may be applied along the length, width, or in tandem with another dressing 60 or other dressings to protect wound 64.

Figure 11:
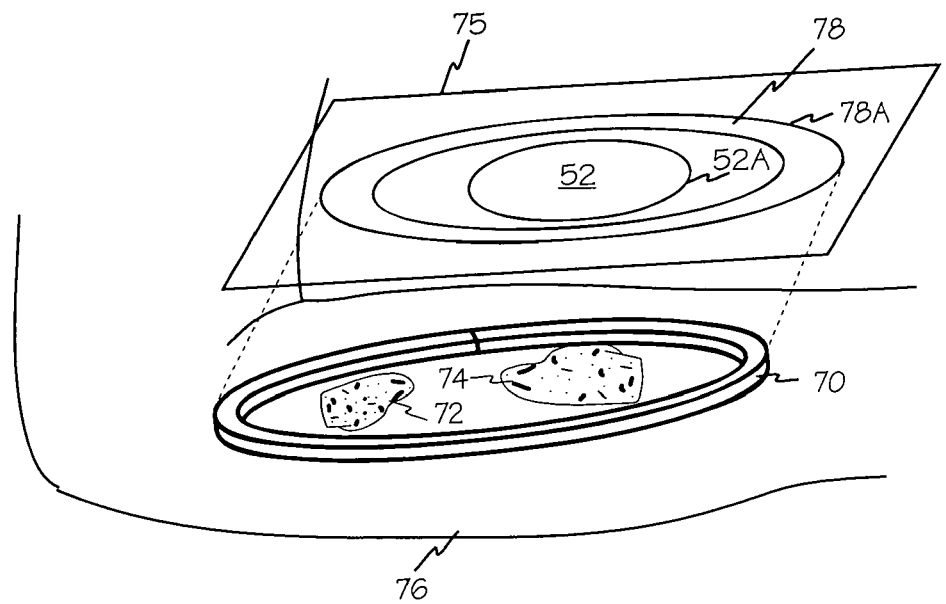
FIG. 11 is a perspective view of a conformable wound frame surrounding two proximately located wounds on the forearm.

Referring now to FIG. 11, conformable frame 70 may be used to protect one or more proximately located wounds such as wounds 72 and 74 on forearm 76. Dressing 78 may be separated from scored dressing sheet 75 which may have one or more dressings scored into sheet 75. Dressings such as dressing 52 or dressing 78 may be separated from sheet 75 along scoring 52A or 78A respectively. Any size or number of dressings may be pre-scored into a dressing sheet such as sheet 75.

Figure 12:
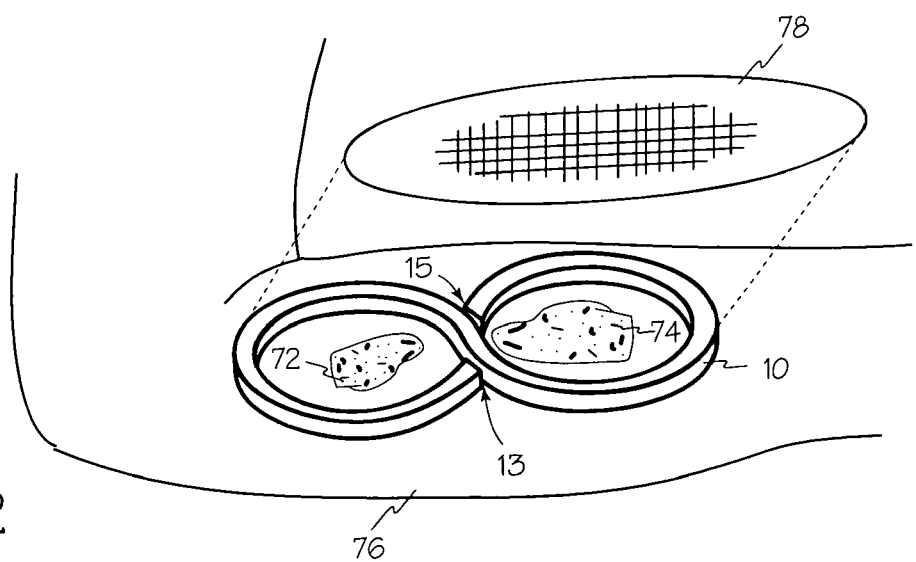
FIG. 12 is a perspective view of an alternate configuration of a conformable wound frame surrounding two proximately located wounds on the forearm.

In an alternate configuration shown in FIG. 12 the connection of first end 13 and second end 15 is transected by conformable frame 10. The use of a FIG. 8 shape provides dressing and pressure support between wounds 72 and 74. To prevent exudate from flowing away from wounds 72 and 74 first end 13 and second end 15 may contact or otherwise engage side 14 and side 16 respectively.

A conformable frame according to the present disclosure may not always completely circumscribe a wound. For wounds positioned in awkward body locations, such as the elbow and knee or for any other reason, a conformable frame may be cut into two or more suitable lengths or frame elements. The frame elements may be positioned around the wound as discussed above. Such manipulation may allow positioning of a dressing without contacting the wound.

In certain circumstances health care professionals may recommend the airing of the wound, i.e., not covering the wound with any dressing. As such, a conformable frame according to the present disclosure may be used to simply protect the wound from physical contact with other foreign objects, such as clothing or bed sheets. This configuration may also be suitable for treatment of any pressure or abrasion sores some of which may be caused by long-term immobility. Conformable frame may be used to surround such sores and relieve the local pressure and permit the sores to heal.

For patients allergic to medically approved adhesives, the conformable frame may be provided without adhesive or, alternatively, with adhesive only on surface 12. In such circumstances, conformable frame 10 must be secured to the wound site with sufficient and appropriate pressure to engage conformable frame 10 with the wound site.

For wound configurations such as illustrated in FIG. 11, particularly large wounds, structurally weak dressings or high pressure wound or sore sites it may be necessary to provide additional support within the perimeter of a conformable frame to support the selected dressing or relieve external pressure.

Figure 13:
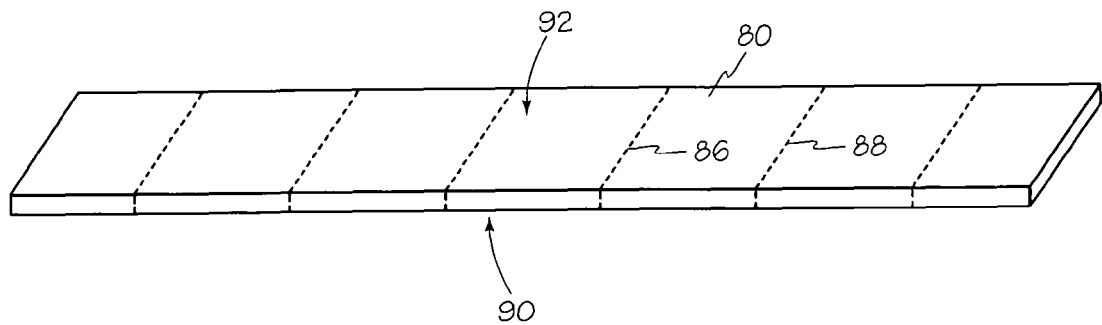
FIG. 13 is a perspective view of a support or bridge member according to the present disclosure.
Figure 15:
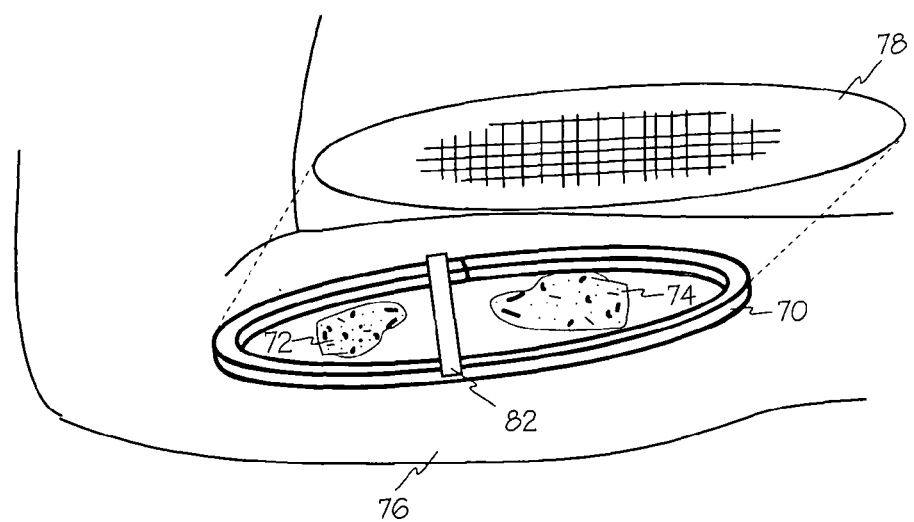
FIG. 15 is a perspective view of a conformable wound frame surrounding two proximately located wounds on the forearm.

Referring now to FIG. 13, one or more bridge members such as bridge member 80 may be used with the conformable frame of the present disclosure to provide additional wound protection. A bridge member may be used with wounds having large surface area or with dressings having little structural strength, or in situations where pressure may be applied to the center of the wound area. Positioning of one or more bridge members such as bridge 82 on conformable frame 70, as depicted in FIG. 15, may prevent dressing 78 from sinking and touching wounds 72 or 74.

A bridge member can have any suitable shape including straight or curved edges, ends or separations. A bridge may also be constructed from inexpensive medical grade rigid plastic polymers, metal or wood particularly conditioned for medical use. Such material may be structurally adapted to allow breakage or separation along segment lines such as lines 86 and 88.

Medical grade adhesive may also be applied to second surface 90 which will come in contact with the conformable frame. A thin layer of film or strip removable at time of use may cover the adhesive as discussed above with respect to the conformable frame. Alternatively, bridge member 80 may have adhesive on both second side 90 and first side 92 to adhere not only to the conformable frame, but also to the dressing.

Figure 14:
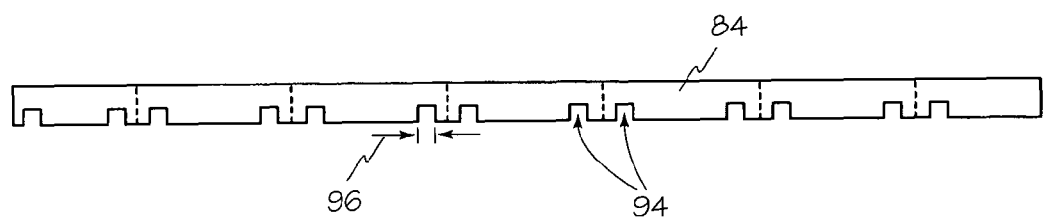
FIG. 14 is a side view of an alternate support or bridge member according to the present disclosure.

Referring now to FIG. 14, alternate bridge member 84 includes a plurality of slots 94. Each slot or opening such as slot 94 may have any suitable shape and dimension providing that width 96 is sized to permit engagement of a suitable conformable frame in the slot.

Figure 16:
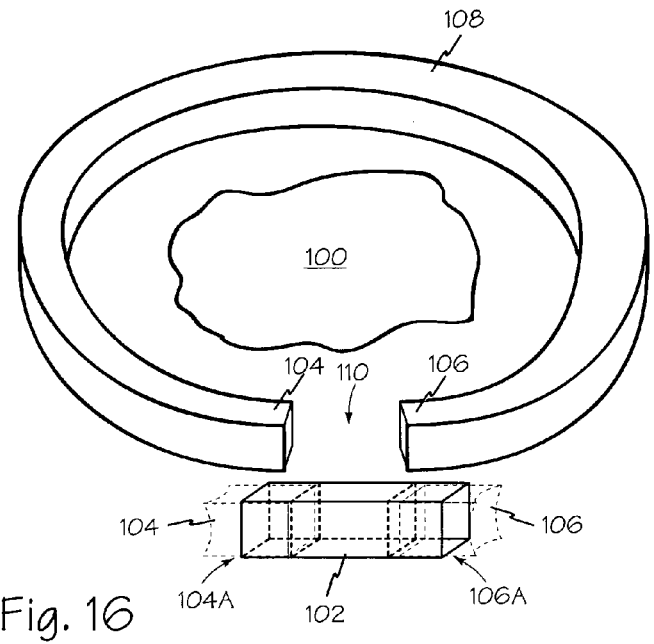
FIG. 16 and 16A are perspective views of connectors used in conjunction with a conformable member.

Referring now to FIG. 16, a connector such as connector 102 may be used to join ends 104 and 106 of conformable frame 108 and provide complete closure around a wound such as wound 100. Any suitable connector such as connector 102 may be used in circumstances where it is desirable not to apply any adhesive to surfaces of conformable frame 108, or where repetitive engagement and disengagement of first and second ends 104 and 106 make adhesive impractical. Lack of adhesive provides the opportunity for first end 104 and second end 106 to move away from one another and create an opening 110. As can be appreciated, exudate from wound 100, if any, may diffuse away from wound 100 through opening 110 and onto other body surfaces.

Connector 102 may be used to close opening 110 by indirectly connecting first end 104 and second end 106. Connector member 102 may be hollow, and may be constructed from any suitable material, including those used for construction of conformable frames. Engagement receptacles 104A and 106A may be slightly larger than the dimensions of first end 104 and second end 106 respectively. This permits conformable frame 108 to be inserted into connector member 102.

Receptacles 104A and 106A should provide secure engagement to first end 104 and second end 106 respectively. Any other suitable configuration may also be used. Connectors such as connector 102 may also be used to connect two or more conformable frames.

Figure 16A:
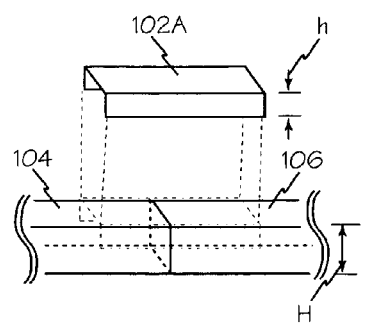

Alternative connector 102A is illustrated in FIG. 16A reinforcing the connection between first end 104 and second end 106. Height h of connector 102A may be about one half height H of conformable frame 108.

Figure 17:
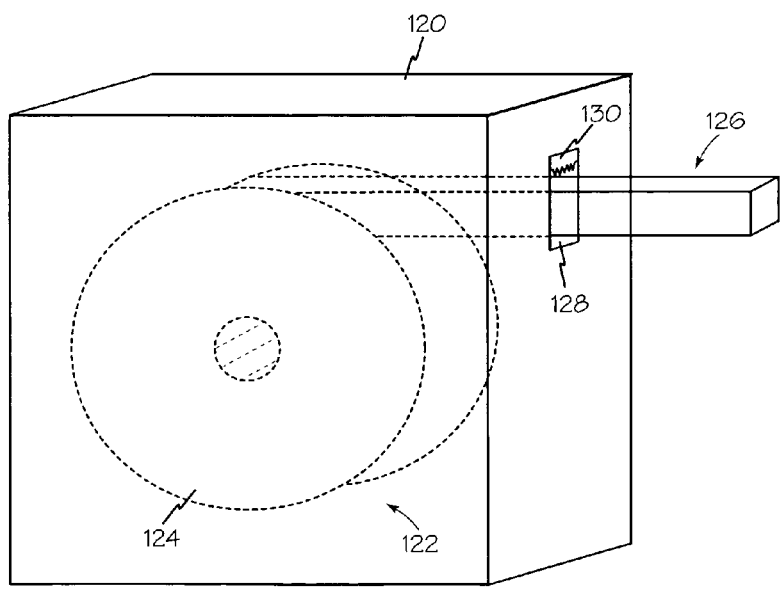
FIG. 17 is a perspective view of a dispenser according to the present disclosure.

Referring now to FIG. 17, conformable frames such as conformable frame 10, conformable frame 34 and others may be stored and dispensed from any suitable dispenser. For example, dispenser 120 may contain one or more coils such as coil 122 wound around a reel or hub 124. Segment 126 may be a portion of conformable frame from coil 122 that is withdrawn through outlet 128. Segment 126 may be pulled out from outlet 128 and cut to a desired length with scissors, or via one or more blades 130 positioned adjacent outlet 128.

Alternatively, a dispenser may be sterilized, and or may have several outlets allowing it to contain several coils containing conformable frames having different dimensions and or characteristics. The number of coils or outlets contained in a dispenser are examples provided for discussion purposes only and should not be viewed as a limitation.

Figure 17A:
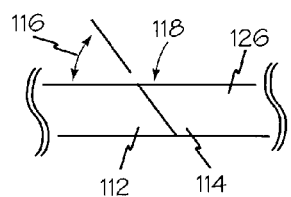
FIGS. 17A and 17B are top views of conformable frame joints formed using the dispenser of FIG. 17.

Referring now to FIG. 17A, conformable frame segment 126 is separated from dispenser 120 forming first end 112 and second end 114. During separation of segment 126 first end 112 and second end 114 were cut, scored or otherwise separated to form angle 116 with exterior side 118. Decreasing angle 116 increases the surface of the first and second end enabling greater engagement. A first end and second end may be cut to similar angled, complementary angles or different angles. Alternatively, first end 112 and second end 114 may be precut or otherwise prepared in standard lengths with assorted end profiles.

Figure 17B:
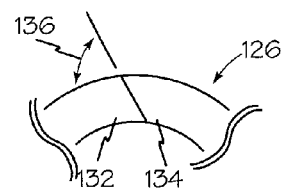

Referring now to FIG. 17B, first end 132 and second end 134 may be cut at a different angles 136 to simplify joining the first and second ends and form curves or shapes having small radii.

In use, a second conformable frame may be positioned on the superficial surface of a first conformable frame. This configuration may be used in situations where a greater protective height around a wound is preferable. A stacked assembly may include more than two conformable frames.

Referring now to FIG. 18, conformable frame 140 may have many different cross sectional dimensions as well as constituent configurations. Conformable frames as discussed above may adopt any suitable geometry. For some applications it may be useful for a conformable frame to be composed of two or more internal layers such as layers 150 and 152 illustrated in FIG. 19. For example, layer 150 may be absorbent, or may include any suitable antibiotic such as for example silver metal and or its salts. Layer 152 may be made from any suitable material.

In some situations it may be preferable to change one or more layers closest to a wound when the layer or layers become saturated or otherwise unsuitable to remain close to the wound. Layer 150 may also be removable to permit changing one or more layers. A scaffold or other suitable apparatus such as scaffold 138 may be secured to exterior layer 152. Internal layer 150 may be secured or otherwise engaged to either or both layer 152 and scaffold 138.

Alternatively, internal layer 150 may be positioned using scaffold 138. Securing layer 150 to layer 152 and scaffold 138 using water soluble adhesive would simplify removal of layer 150 and may also serve to identify a saturated layer as it separates from the structural layer and the scaffold. If layer 150 needed to be changed, any dressing or lid applied over conformable frame 140 may be disengaged. Layer 150 may be removed and a replacement layer may be inserted using scaffold 138 as a guide and engagement mechanism.

Referring now to FIG. 19A, an alternate scaffold 139 may include lip 141 to frictionally engage layer 150 without the use of adhesive or other bonding agent. Scaffold 138 and or scaffold 139 may also include holes or other suitable openings such as holes 135 and 143 and openings 145 in shelf 133 and or lip 141 as illustrated in the associated close-up bottom views. Lip 141 may also permit usage and of any suitable absorbent material in a non-contact position relative to the wound. The absorbent material may be frictionally engaged by lip 141 and supported by scaffold 139.

Some materials may have directional characteristics, and when combined in multiple layers may offer unique benefits. Many additional characteristics may also be useful, for example, layer 156 of FIG. 20 may be absorbent to absorb and retain exudate from the wound, and layer 154 may be formed of a material providing dimensional stability or structural integrity.

Similarly, referring to FIG. 22, layer 164 may be absorbent and layer 166 may provide structural integrity and layer 166 may enclose layer 164 to prevent exudates from wound side 144 transiting conformable frame 140 and exiting through exterior side 146. Any suitable material may be selected for each layer. Layer 168 may be any suitable material.

Referring now to FIG. 21, layers 158, 160 and 162 may also provide one or more diagnostic indicators such as for example, ph level, temperature, moisture level, $O^2$ levels or any other suitable parameter. The state of the parameter may be indicated by one or more color states of one or more layers.

Referring now to FIG. 23, conformable frame 170 may include one or more internal layers such as layers 172, 174 and 176 and one or more absorbent appendages such as arm 178. Arm 178 and layer 176 may be composed of any suitable material for absorbing exudates from wound 180. The physical geometry of arm 178 may vary for varying applications. For example, arm 184 shown in FIG. 24 provides vertical relief from wound 180.

Alternatively as illustrated in FIG. 25, flexible absorbent appendages may also be secured to a conformable frame such as conformable frame 192. Absorbent appendages 194 may be provided to absorb exudate from wound 180. Any suitable material or combination of materials may be used as appendages 194 such as for example natural fibers such as cotton or any suitable man-made fiber. Any other suitable configuration may also be employed such as enclosing one or more cotton balls or gauze within the space enclosed by a conformable frame and a covering dressing.

Figure 26:
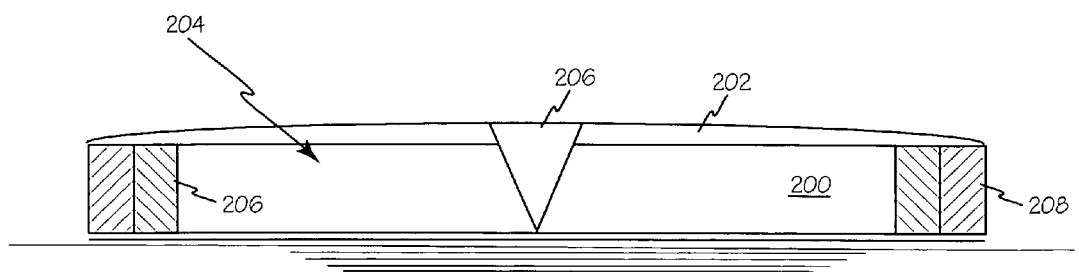
FIG. 26 is a cross section of an alternate conformable frame and lid configuration.

Referring now to FIG. 26, conformable frame 200 may also be used with a cover or lid 202 to provide a controlled environment in enclosed space 204 adjacent a wound site. Lid 202 may be removably engaged to conformable frame 200 using any suitable technique such as frictional or adhesive engagement. Lid 202 may be formed of any suitable material or combination of materials such as a structural grid layer with one or more laminate layers to obtain suitable performance and moisture transmission/retention.

Alternatively, lid 202 may also include one or more absorptive elements such as cone 206 for removing moisture or exudate from wounds such as wound 210. Absorptive elements may have any suitable shape or dimension and may be formed of any suitable material. For example, cone 206 may be formed of material that is selectively absorbent to remove exudate and unwanted fluids.

Figure 27:
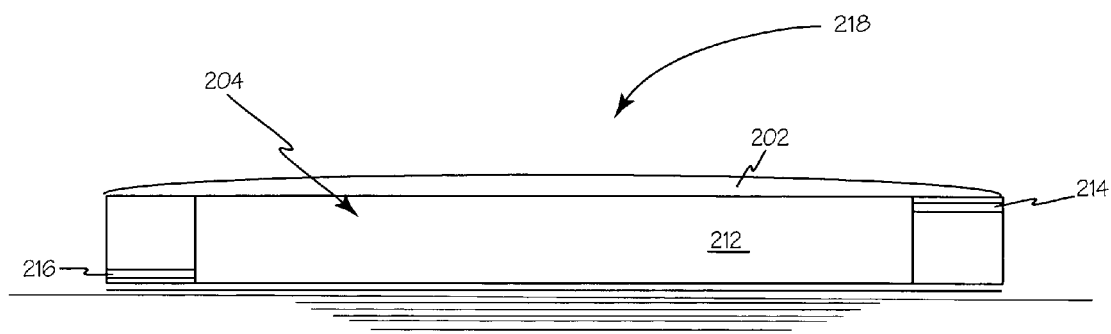
FIG. 27 is a cross section of another alternate conformable frame and lid configuration.

Enclosed space 204 may be further controlled as illustrated in FIG. 27. Conformable frame 212 may include one or more access ports such as inlet port 214 and outlet port 216. Use of access ports permits irrigation, treatment, and or debridement of wound 210 without removing wound protection shield 218. Fluid or other material may be introduced into enclosed space 204 through inlet port 214. In the case of used fluid or exudate, removal may be accomplished using outlet port 216. Access ports such as inlet port 214 and outlet port 216 may be reclosable to secure enclosed space 204. Alternatively, conformable frame 212 may be formed of material that permits a syringe to be inserted through the conformable frame for insertion of material or to remove material. Access ports may also be formed in the cover or lid 202.

Figure 28:
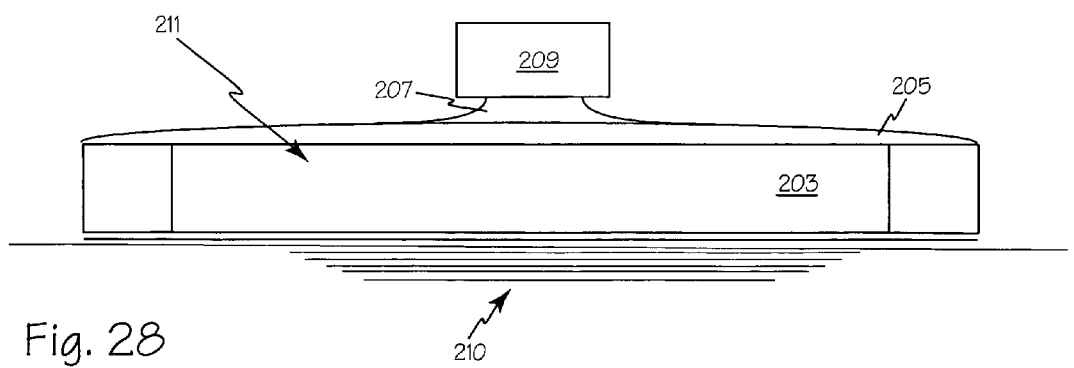
FIG. 28 is a cross section of a conformable frame with a vacuum lid configuration.

Referring now to FIG. 28 enclosed vacuum space 211 may be created and maintained by the use of a suitable cover or lid such as vacuum lid 205. A partial or complete vacuum may be created in space 211 by vacuum device 209 through adapter 207 or through a conformable frame such as conformable frame 212 using inlet port 214 or outlet port 216. Using a conformable frame and specifically adapted lid such as lid 205 may permit a vacuum device such as vacuum device 209 to be located on lid 205 without creating unsatisfactory pressure on or adjacent wound 210. Lid 205 may require an adapter such as adapter 207 or lid 205 may be specifically formed to adapt to a vacuum device or connector to a vacuum device to create a full or partial vacuum within space 211.

Figure 29:
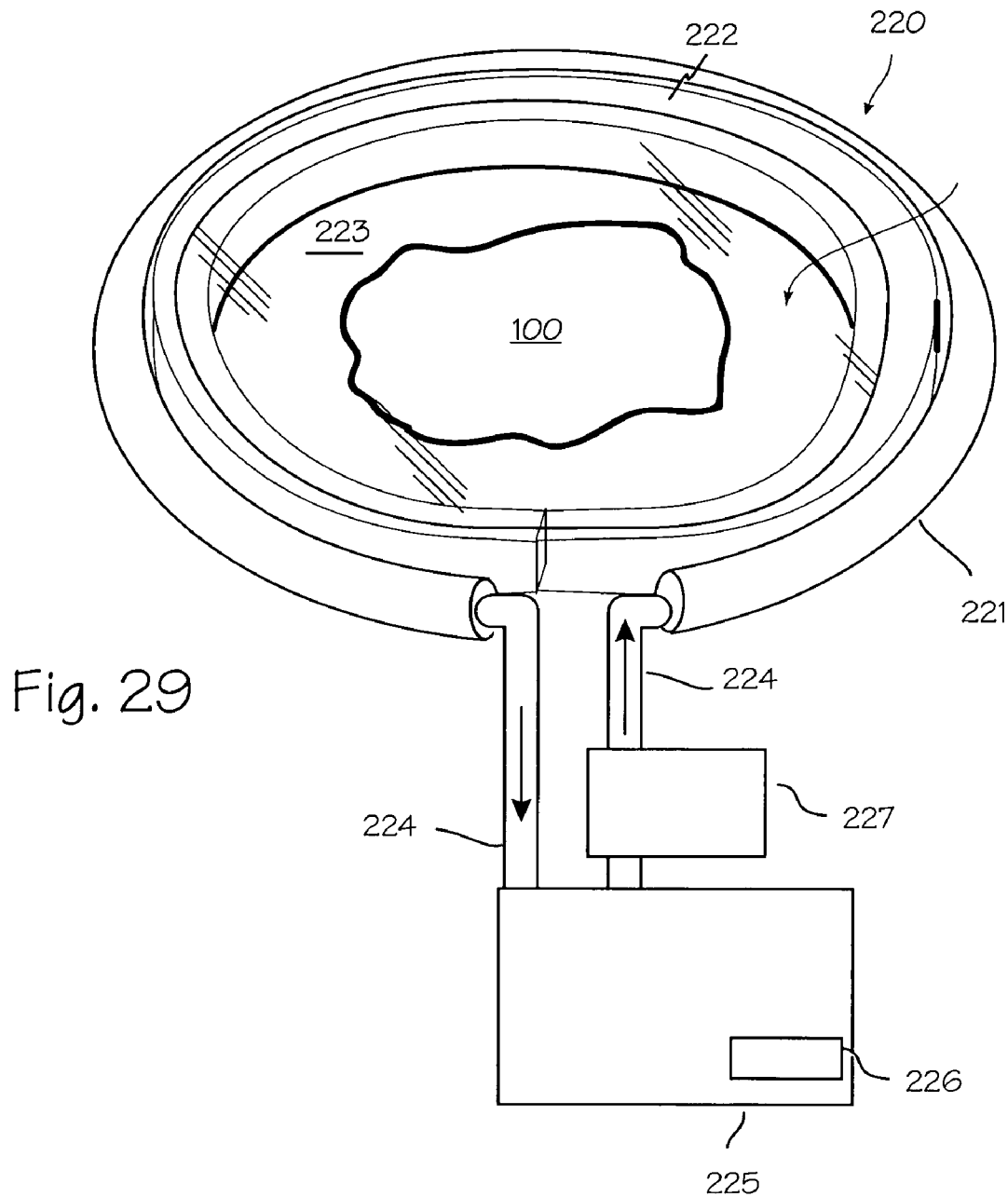
FIG. 29 illustrates a device for isolating a wound and providing heat to the wound to encourage healing.

FIG. 29 illustrates the wound isolation and warming device 220, including the conformable tube 221, inner absorbent ring or strip 222 and breathable vapor barrier 223. The tube and absorbent strip are provided with any suitable adhesive on the cutaneous surfaces of the tubing, the strip, or both, to secure the device to the skin of a patient. The conformable tubing is made of polyethylene or other thermally conductive material, and is preferably conformable to the extent that it may either be bent and formed as necessary to conform to the contours of a patient's body, though it may be supplied in straight lengths or in coils. The device also includes water supply and return conduits 224, and a warm water source 225 comprising a water reservoir, heater 226 (or any other suitable heating means), pump 227, and appropriate thermostats, heating regulators and flow regulators. Pulsatile flow can be provided with roller pump or centrifugal pulsatile flow pump. The heater and thermostat are preferably operable to maintain water temperature at a therapeutic temperature between about 36°-39° C., but may be operated to maintain higher or lower temperatures as medically indicated. The device is illustrated in place surrounding wound 100 on the skin of a patient.

Figure 30:
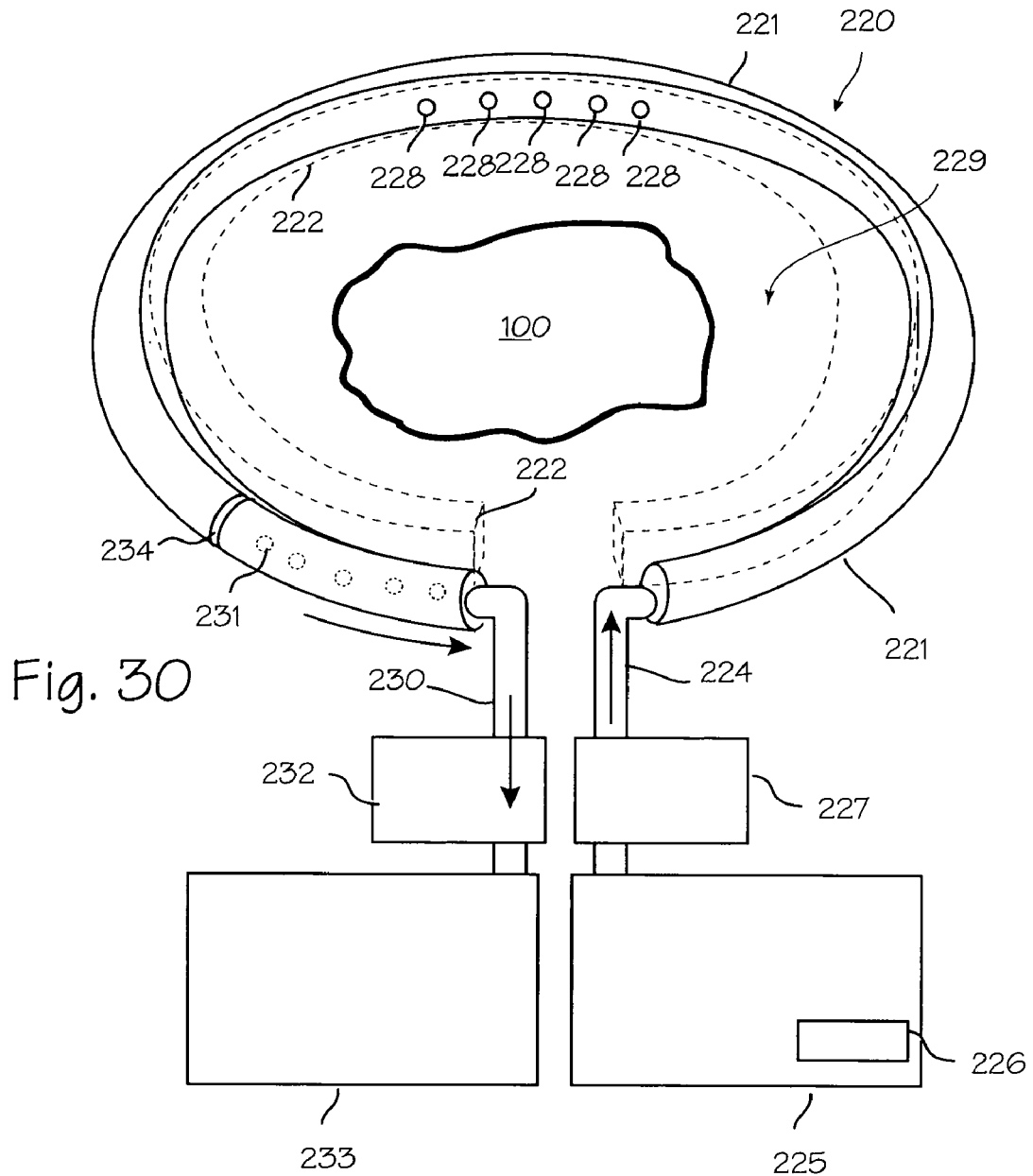
FIG. 30 illustrates the device of FIG. 29 modified to provide fluid flow over the wound to encourage healing.

The device may be modified as shown in FIG. 30, in which the tube 221 in the vicinity of the wound is perforated, such that apertures 228 distributed along the inner wall of tubing 221 and any intervening portion of conformable frame 222 direct water into the interior space 229 (defined by the conformable frame) and onto the wound. Water is collected through return tube 230 through suction ports 231 and appropriate suction pump 232 and collected in wastewater tank 233. Water may be collected through a discrete segment of the tube formed integrally with an interior wall or plug 234 provided to isolate the supply and suction tubes. Alternatively, the suction tube may be butt-joined with the supply tube. Used fluid may also be collected with a second, discrete suction tube, or through an additional lumen and ports in the first tube. Tube 221 may be made or formed in any cross section shape including but not limited to cylindrical, rectangular, trapaziodal or any other suitable shape. A suitable shape of tube 221 may be selected to control the flow of thermal energy around the wound, generally to increase the temperature of the wound site, however cooling may also be provided. Tube 221 may also include one or more insulating layers to control the thermal energy and prevent unwanted losses. Adhesive may also be used as necessary on tube or its adjacent surfaces to secure tube 221 in use.

In use, the devices of FIGS. 29 and 30 are applied to a patient so that the conformable tubing substantially circumscribes a wound, and fixed to the skin of the patient with adhesives on the cutaneous surfaces of the conformable tubing and absorbent ring (or secured with bandages, wherever adhesives are inadequate or inappropriate). The pump and heater are operated to maintain warm fluid flow through the tube, to maintain a warm environment proximate the wound. In the closed system of FIG. 29, the fluid is returned to reservoir, reheated and re-circulated through the system. When using the device of FIG. 30, the suction pump is operated to draw fluid from the wound environment and deliver that fluid to the wastewater tank. Therapeutic agents such as antibiotics may be added to the warm water source when medically indicated.

Figure 31:
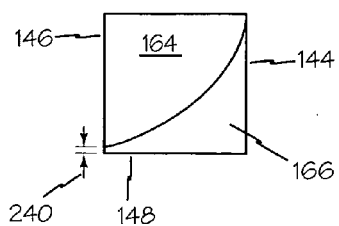
FIG. 31 is another still alternate cross section of the conformable frame of FIG. 18.

Referring now to FIGS. 31, absorbent layer 164 may be reoriented to be out of contact with the patients skin. Absorbent layer 164 may be configured to absorb and store exudate from a wound. Relief such as relief 240 isolates the absorbed exudate away from the patients skin. Relief 240 may be selected to be any suitable dimension.

Figure 32:
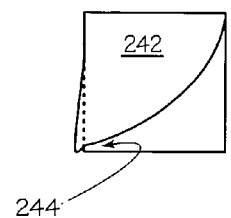
FIG. 32 is yet another still alternate cross-section of the conformable frame of FIG. 18.

Dynamic exudate management and removal may be provided by layer 242 of FIG. 32. The material of layer 242 is selected to flex when new and to extend over relief 244 and contact the surface of a wound to engage exudate. Upon absorbing exudate, layer 242 will contract to draw exudate across relief 244 to continue wicking exudate from the wound with absorbent layer 242 out of contact with the wound or the patients skin.

Figure 33:
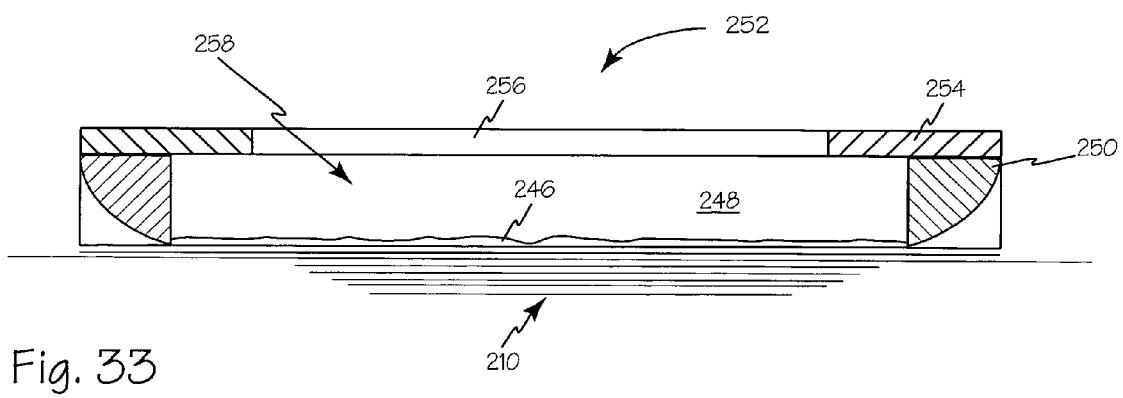
FIG. 33 is a cross section of yet another alternate conformable frame configuration with an absorbent dressing.

Referring to FIG. 33, exudate 246 may be conducted from wound 210 and enclosed space 258 with alternate conformable frame 248. The material of layer 250 may be selected to perform as a conduit by drawing exudate 246 from wound 210 and transferring exudate 246 to one or more storage layers of dressing 252 such as layer 254. Layer 250 will not retain exudate 246. Absorbent layer 254 may be any suitable material and may also be expandable. Area 256 of dressing 252 may permit viewing of wound 210 and may have a selected permeability to enhance control of enclosed space 258.

Figure 34:
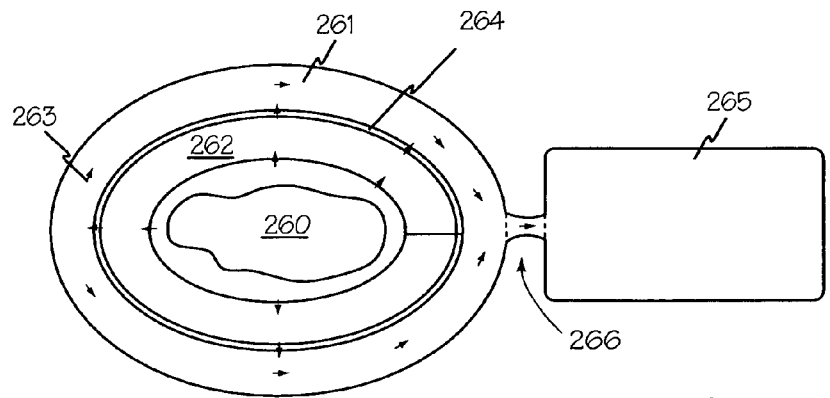
FIG. 34 is a cross section of an alternate conformable frame configuration including exudate capture and storage.
Figure 35:
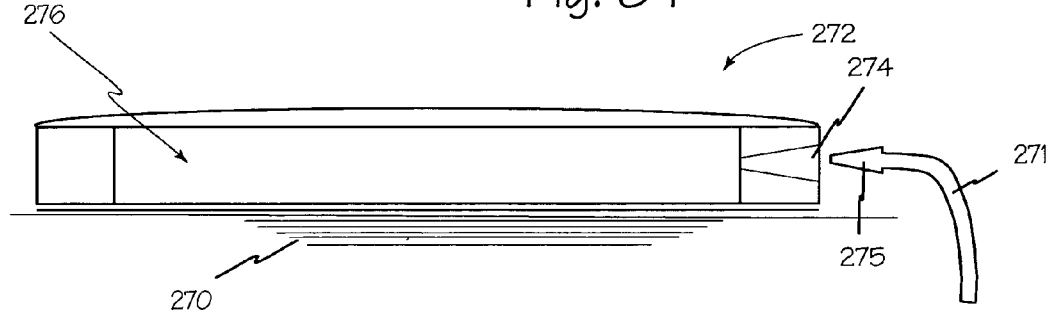
FIG. 35 is a cross section of an alternate conformable frame configuration including exudate removal apertures and removal apparatus.

Wound 260 of FIG. 34 may produce exudate 263. An alternate conformable frame 262 may conduct exudate away from wound 260. Membrane 264 may surround conformable frame 262 or may otherwise be included as a layer of conformable frame 262. Membrane 264 may allow exudate to pass in only one direction, away from the wound. Once exudate 263 has passed membrane 264 it may be absorbed or otherwise conducted along drain 261 away from the wound. Drain 261 may include an access port 266 which may accommodate continuous or intermittent connection for withdrawal or drainage of exudate from drain 261 into reservoir 265. Reservoir 265 may be adjacent to wound 260 or may be remotely located by interconnecting reservoir 265 to drain 261 with a tube or other suitable element. Alternatively, reservoir 265 may be used to introduce water or other suitable solvent or cleanser into drain 261 to expedite removal of exudate 263.

Use of access ports permits exudate management with irrigation, treatment, and or debridement of a wound such as wound 270 without removing wound protection shield 272. Fluid and or other material may be introduced, and exudate, fluid and or other material may be removed from enclosed space 276 through port 274. Access ports such as port 274 may adopt any suitable geometry for engaging various tubes, such as tube 271, syringes, and devices such as reservoir 273. Ports may be reclosable using any suitable technique to secure enclosed space 276.

Adapters such as adapter 275 may engage port 274 to permit leak proof access to enclosed space 276. As adapter 275 enters port 274 the port is opened, and as adapter 275 is withdrawn port 274 closes and withdrawal of an adapter cleanses port 274.

Figure 36:
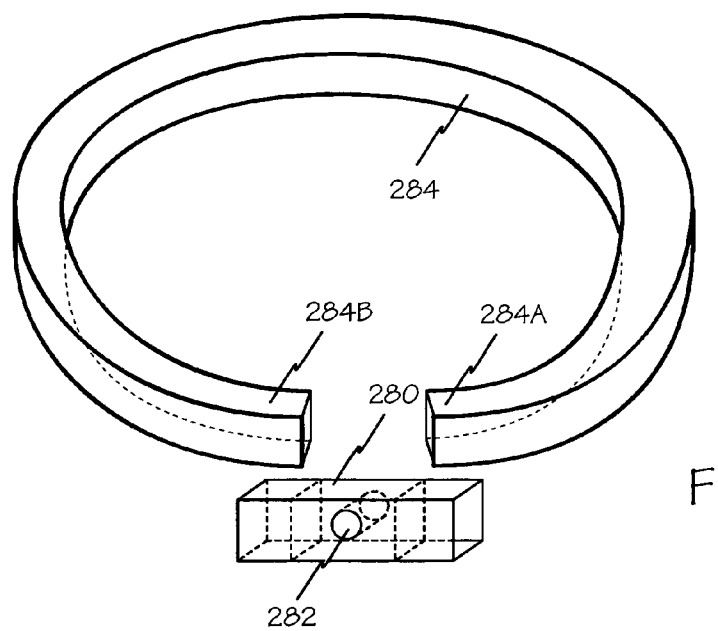
FIG. 36 is a perspective view of a conformable frame with an alternate connector for joining the ends of the conformable frame.

Alternatively, one or more access ports such as access port 282 may also be included in connectors such as connector 280 of FIG. 36. Connector 280 may be used to engage ends 284a and 284B of conformable frame 284.

Figure 37:
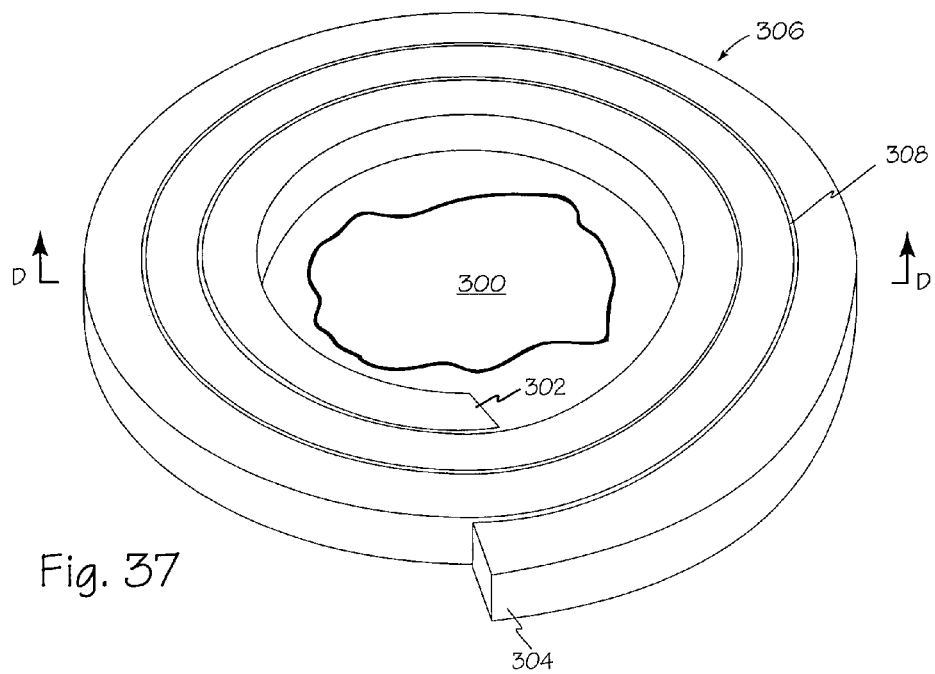
FIG. 37 is a perspective view of an alternate deformable wound frame spiral wrapped according to the present disclosure.

Referring now to FIG. 37 conformable frame 306 may be wrapped one or more times around a wound such as wound 300 forming a spiral frame. This application permits fast application of conformable frame 306. First end 302 is applied to a location adjacent the wound and conformable frame 306 is wound around the wound until the conformable frame has circumscribed the wound and the remainder of the conformable frame is applied in a spiral with outer edge 303 of the applied frame in contact with inner edge 301 of the adjacent wrap forming joint 308. This application increases the surface area of conformable frame in contact with the patient to distribute pressure applied to the wound area to a greater area of the patient's body, and at a greater distance from the actual wound.

Figure 38:
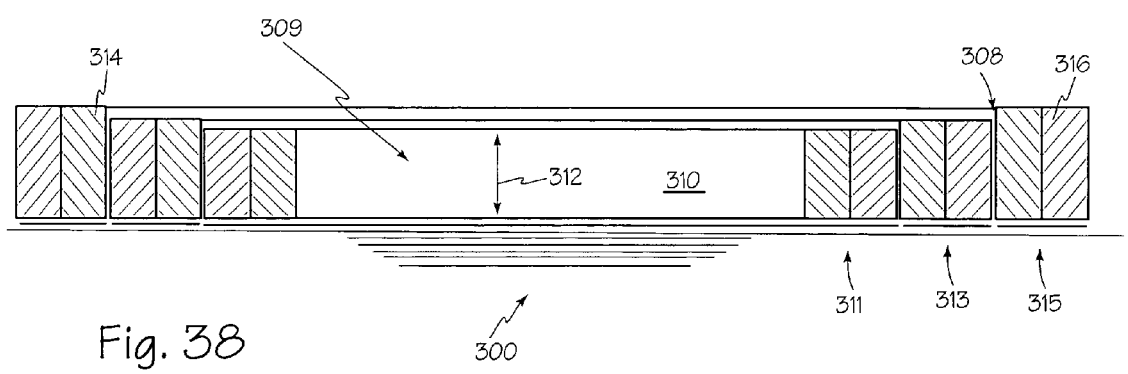
FIG. 38 is a cross section of the conformable frame of FIG. 37 taken along D-D.

Referring now to FIG. 38, a conformable frame spiral may be formed using a frame having a constant height 312. Alternatively, height 312 may vary from first end 302 to second end 304 resulting in a cross-section as shown. Inner wrap 311 has the lowest height 312 and subsequent wraps such as wraps 313 and 315 have increasing heights. The height variations may be distinct such as steps, or it may be gradual and continuous. The height variations distribute pressure that might otherwise impact the wound, to surrounding tissue removed from the wound. As pressure increases compressing outer wraps of conformable frame 310, the inner wraps begin to provide support increasing pressure resistance. Conformable frame 310 may be formed of one or more layers 314 and or 316 as discussed above.

Figure 39:
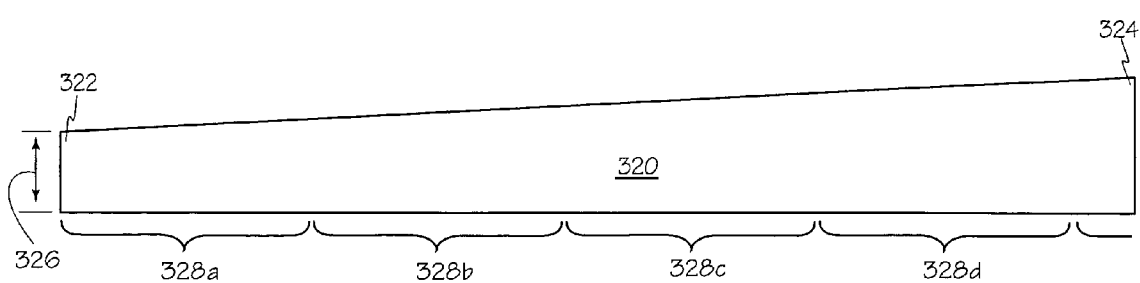
FIG. 39 is a side view of another alternate deformable wound frame according to the present disclosure.

Conformable frame 320 of FIG. 39 illustrates a continuously increasing height from first end 322 to second end 324. Characteristics of conformable frame 320 may change gradually and continuously from first end 322 to second end 324 or there may be one or more zones such as zones 328a, 328b, 328c and or 328d. Each zone may have different compression resistance, absorbance or any other suitable characteristics.

Conformable frame 408 of FIG. 40 may be spiral wrapped around wound 400 as discussed above. Conformable frame 408 may include one or more areas of absorbent material such as areas 401. Non-absorbent sections 406 may separate absorbent areas 401. This configuration prevents absorbed exudate and or other fluids from leaking from conformable frame 408. If conformable frame 408 is used with an absorbent cover, bandage or other top, absorbent areas 401 in outer wraps may operate as additional exudate storage without direct access to wound 400.

In situations in which a wound may require frequent observation or dressing changes and or the skin or other tissue surrounding a wound is sensitive to repeated adhesive removal, a conformable wound substrate such as substrate 410 may be used as shown in FIGS. 41, 42 and 43. Conformable substrate 410 may be stored, dispensed, cut and formed as discussed above for conformable frames. Conformable substrate 410 may be thin, having for example a vertical dimension 411 from 0.1 mm to 6 mm and a width 412 that is generally 10 to 100 times height 411. Any suitable dressing or other adhesive cover, shield or frame may be secured to superficial side 424.

With conformable substrate 410 surrounding wound 400, a dressing such as dressing 420 may be applied over the wound with the dressing adhesive 422 securing the dressing to superficial side 424 of wound substrate 410. In use, dressings may be repetitively applied and removed from conformable substrate 410 surrounding wound 400 without repetitive insult to the tissue surrounding wound 400. Dressings or other covers over wound 400 may be removed based on time or wound circumstances such as exudate removal, wound debridement or cleaning, or other suitable rationale. Substrate adhesive 418 is applied to adhesive side 418A and may be any suitable adhesive. In practice adhesive 418 may be selected to provide secure attachment for a preselected time, for example, seven days. At the end of the preselected time the adhesive will breakdown and release the substrate from the patients skin without any additional force or trauma to the patients skin 415 surrounding wound 400.

Alternatively, adhesive 418 may be selected to require application of a suitable release agent to remove the substrate from the patient. Thus, dressings, conformable frames or other suitable wound coverings may be repetitively applied and removed from the substrate based on time or wound circumstances and the substrate will protect the patient's skin 415 and will not release until a suitable release agent is applied to adhesive 418.

The material used to form substrate 410 may be selected to enable the substrate to be formed around a wound such as wound 400 and have outer edge 414 stretch relative to inner edge 416 and inner edge 416 to stretch relative to outer edge 416 and thus conform to patients skin 415. Adhesive layer 418 may be selected to firmly attach substrate 410 to skin 415 with outer edge 414 stretched relative to inner edge 416.

Figure 44:
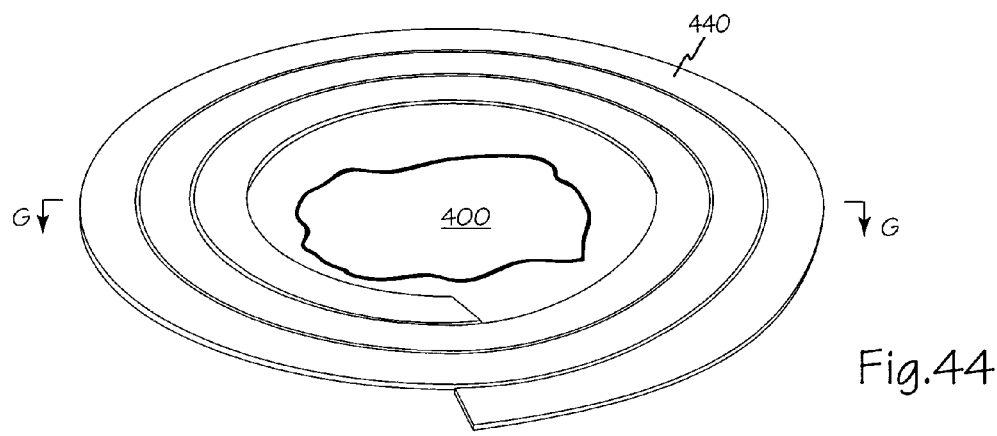
FIG. 44 is a perspective view of an alternate conformable wound substrate according to the present disclosure.
Figure 45:
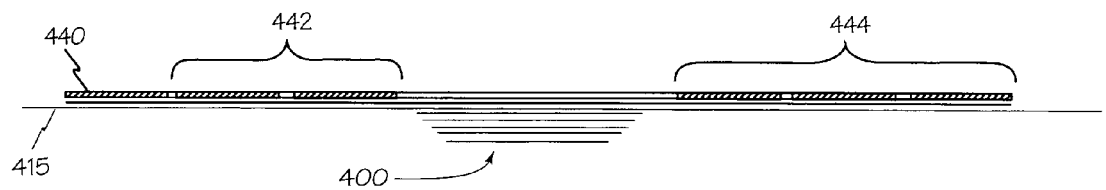
FIG. 45 is a cross section of the conformable substrate of FIG. 44 taken along G-G.

In FIG. 44 and FIG. 45 conformable substrate 440 may be spiral wrapped around wound 400. This technique provides increased skin shielding using only a single substrate and a simple application technique. The surface area of a patient's skin 415 that may be protected from repetitive dressing insult may be doubled 442, tripled 444 or more depending on the number of circumferential wraps of the substrate about a wound. This may be necessitated by a desire to have a low profile dressing that does not contact the wound surface and extra tension is required to prevent contact between the dressing and the wound.

Figure 46:
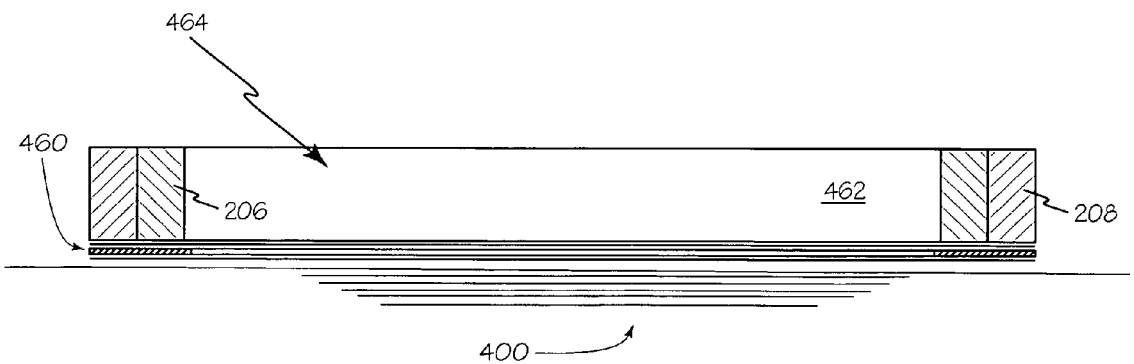
FIG. 46 is a cross section of a conformable substrate applied around a wound in conjunction with a conformable frame.

FIG. 46 provides an example of a conformable substrate 460 used in combination with a conformable frame 462 to form and control space 464 adjacent wound 400. In this configuration, dressings may be applied and removed over conformable frame 462 for wound care and exudate management. Conformable frame 462 may include any suitable exudate absorbing and wicking characteristics as discussed above. Conformable frame 462 may be applied and removed from conformable substrate 460 for wound care and exudate management without disturbing or traumatizing patient skin 415 adjacent wound 400. Both conformable frame 462 and conformable substrate 460 may be spiral wrapped around wound 400 as discussed above.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A wound care apparatus comprising:
   a conformable wound substrate configured to circumscribe a wound;
   a layer of adhesive configured to be disposed between the substrate and a patient's skin to adhere the substrate to the skin;
   an elongated conformable frame configured to be wrapped around the wound in an overlapping, spiral fashion to thereby define a wound space adjacent the wound;
   a cover engaging the conformable frame and configured to enclose the wound space; and
   an additional layer of adhesive disposed on a lower surface of the elongated conformable frame.

2. The wound care apparatus of claim 1 wherein the conformable frame comprises an exudate absorbing material.

3. The wound care apparatus of claim 2, wherein the substrate comprises a non-absorbent material.

4. The wound care apparatus of claim 1, wherein the cover comprises a medium for exudate storage.

5. The wound care apparatus of claim 1, wherein the conformable substrate comprises an elongated strip wrapped around the wound in a spiral.

6. The wound care apparatus of claim 1, wherein the elongated conformable frame comprises a strip of polyurethane foam.

7. The wound care apparatus of claim 1, wherein the elongated conformable frame has a length and a height, wherein the height is uniform along the length.

8. The wound care apparatus of claim 1, wherein the elongated conformable frame has a length and a height, wherein the height varies gradually and continually along the length.

9. The wound care apparatus of claim 1, wherein the elongated conformable frame includes a non-absorbent material and an absorbent material.

10. The wound care apparatus of claim 1, wherein the substrate has a width and a height, wherein the width is from 10 to 100 times the height.

11. The wound care apparatus of claim 1, wherein the additional layer of adhesive is disposed between the substrate and the elongated conformable frame and adheres the substrate to the elongated conformable frame.

12. The wound care apparatus of claim 1, wherein the elongated conformable frame is removable relative to the substrate.

13. The wound care apparatus of claim 1, wherein the elongated conformable frame transfers exudate from the wound to the cover.

* * * * *